United States Patent
Slaton et al.

(10) Patent No.: US 7,741,304 B2
(45) Date of Patent: Jun. 22, 2010

(54) CASEIN KINASE 2 ANTISENSE THERAPY

(75) Inventors: Joel W. Slaton, Minneapolis, MN (US); Khalil Ahmed, Minneapolis, MN (US); Gretchen M. Unger, Chaska, MN (US); Alan Davis, Lakeville, MN (US); Dan Sloper, Maplewood, MN (US)

(73) Assignee: Regents of The University of Minnesota, Saint Paul, MN (US)

( * ) Notice: Subject to any disclaimer, the term of this patent is extended or adjusted under 35 U.S.C. 154(b) by 39 days.

(21) Appl. No.: 11/763,366

(22) Filed: Jun. 14, 2007

(65) Prior Publication Data

US 2008/0113932 A1 May 15, 2008

Related U.S. Application Data

(63) Continuation-in-part of application No. PCT/US2005/045820, filed on Dec. 14, 2005.

(60) Provisional application No. 60/636,299, filed on Dec. 14, 2004, provisional application No. 60/657,049, filed on Feb. 28, 2005, provisional application No. 60/898,674, filed on Feb. 1, 2007, provisional application No. 60/944,028, filed on Jun. 14, 2007.

(51) Int. Cl.
*A61K 31/70* (2006.01)
*C07H 21/02* (2006.01)
*C07H 21/04* (2006.01)
*C12Q 1/68* (2006.01)
*C12N 5/00* (2006.01)

(52) U.S. Cl. .......................... 514/44; 435/6; 435/375; 435/377; 536/23.1; 536/24.1; 536/24.5

(58) Field of Classification Search .................. None
See application file for complete search history.

(56) References Cited

U.S. PATENT DOCUMENTS

| | | | |
|---|---|---|---|
| 3,687,808 | A | 8/1972 | Merigan et al. |
| 4,469,863 | A | 9/1984 | Ts'o et al. |
| 4,981,863 | A | 1/1991 | Kane et al. |
| 5,214,136 | A | 5/1993 | Lin et al. |
| 5,218,105 | A | 6/1993 | Cook et al. |
| 5,235,033 | A | 8/1993 | Summerton et al. |
| 5,359,044 | A | 10/1994 | Cook et al. |
| 5,489,677 | A | 2/1996 | Sanghvi et al. |
| 5,539,082 | A | 7/1996 | Nielsen et al. |
| 5,596,086 | A | 1/1997 | Matteucci et al. |
| 5,602,240 | A | 2/1997 | De Mesmaeker et al. |
| 5,750,666 | A | 5/1998 | Caruthers et al. |
| 6,440,738 | B1 | 8/2002 | Wyatt |
| 6,455,307 | B1 | 9/2002 | McKay et al. |
| 6,607,916 | B2 | 8/2003 | Freier et al. |
| 6,632,671 | B2 | 10/2003 | Unger |
| 2002/0147163 | A1 | 10/2002 | McKay et al. |
| 2004/0038303 | A1 | 2/2004 | Unger |
| 2007/0219148 | A1 | 9/2007 | Schaack et al. |
| 2008/0220072 | A1 | 9/2008 | Unger et al. |

FOREIGN PATENT DOCUMENTS

| | | |
|---|---|---|
| EP | 1 911 451 | 4/2008 |
| WO | WO 02/24950 | 3/2002 |
| WO | WO 03/87389 | 10/2003 |

OTHER PUBLICATIONS

Faust et al., "Antisense Oligonucleotides Against Protein Kinase CK2-Alpha Inhibit Growth of Squamous Cell Carcinoma of The Head and Neck In Vitro," *Head and Neck*, 2000, 22(4):341-346.
Unger et al., "Protein kinase CK2 as regulator of cell survival: Implications for cancer therapy," *Current Cancer Drug Targets*, 2004, 4:77-84.
Unger et al., "Antisense formulation via sub-50nm nanoencapsulation enhances effective . . ." *Proc. 94th Annual Meeting of American Association for Cancer Research*, Jul. 11-14, 2003, p. 1287.
GenBank Accession NM_001320 dated Dec. 23, 2007, 4 pages.
GenBank Accession NM_001892 dated Dec. 23, 2007, 5 pages.
GenBank Accession NM_009974 dated Jan. 9, 2008, 4 pages.
GenBank Accession S72393 dated Jan. 24, 1995, 7 pages.
GenBank Accession X69951 dated Nov. 14, 2006, 8 pages.
GenBank Accession X70251 dated Nov. 10, 2005, 2 pages.
Aukhil et al., "Cell- and Heparin-binding Domains of the Hexabrachion Arm Identified by Tenascin Expression Proteins," *J. Biol Chem.*, 1993, 268(4):2542-2553.
Cullen, "Enhancing and confirming the specificity of RNAi experiments," *Nature Methods*, 2006, 3(9):677-681.
Faust et al., "Subcellular immunolocalization of protein kinase CK2 in normal and carcinoma cells," *Int. J. Biochem. Cell Biol.*, 1999, 31:941-949.
Guerra et al., "The carboxy terminus of p53 mimics the polylysine effect of protein kinase CK2-catalyzed MDM2 phosphorylation," *Oncogene*, 1997, 14:2683-2688.
Nastainczyk et al., "Isolation and Characterization of a Monoclonal Anti-Protein Kinase CK2 β-Subunit Antibody of the IgG Class for the Direct Detection of CK2 β-Subunit in Tissue Cultures of Various Mammalian Species and Human Tumors," *Hybridoma*, 1995, 14(4):335-339.
Nielsen et al., "Sequence-Selective Recognition of DNA by Strand Displacement with a Thymine-Substituted Polyamide," *Science*, 1991, 254:1497-1500.
Pashley and Karaman, "Surfactants and Self-Assembly" and "Emulsions and Microemulsions," *Applied Colloid and Surface Chemistry*, 2004, John Wiley, Chapters 4 and 5, p. 60-85.
Pei and Tuschl, "On the art of identifying effective and specific siRNAs," *Nature Methods*, 2006, 3(9):670-676.
Pouton et al., "Polycation-DNA complexes for gene delivery: a comparison of the biopharmaceutical properties of cationic polypeptides and cationic lipids," *J. Controlled Release*, 1998, 53:289-299.

(Continued)

*Primary Examiner*—Sean R McGarry
(74) *Attorney, Agent, or Firm*—Fish & Richardson P.C.

(57) ABSTRACT

The invention provides for antisense oligonucleotides that hybridize to casein kinase 2 nucleic acid sequences and methods of using such antisense oligonucleotides to inhibit expression of casein kinase 2 and reduce the size of solid tumors.

21 Claims, 3 Drawing Sheets

OTHER PUBLICATIONS

Rolland, "From Genes to Gene Medicines: Recent Advances in Nonviral Gene Delivery," *Crit. Rev. Therapeutic Drug Carr. Syst.*, 1998, 15(2):143-198.

Sanghvi, "Heterocyclic Base Modifications in Nucleic Acids and Their Applications in Antisense Oligonucleotides," *Antisense Research and Applications*, 1993, CRC Press, Boca Raton, FL, Chapter 15, pp. 273-288.

Slaton et al., "Induction of Apoptosis by Antisense CK2 in Human Prostate Cancer Xenograft Model," *Mol. Cancer Res.*, 2004, 2(12):712-721.

Snøve, Jr. and Rossi, "Expressing short hairpin RNAs in vivo," *Nature Methods*, 2006, 3(9):689-695.

Tawfic et al., "Protein kinase CK2 signal in neoplasia," *Histol. Histopathol.*, 2001, 16:573-582.

Wang et al., "Response of cancer cells to molecular interruption of the CK2 signal," *Mol. Cell. Biochem.*, 2001, 227:167-174.

Wiznerowicz et al., "Tuning silence: conditional systems for RNA interference," *Nature Methods*, 2006, 3(9):682-688.

Ahmad et al., "Targeting CK2 for cancer therapy," *Anti-Cancer Drugs*, 2005, 16(10):1037-1043.

Ulloa et al., "Depletion of catalytic and regulatory subunits of protein kinase CK2 by antisense oligonucleotide treatment of neuroblastoma cells," *Cell. Mol. Neurobiol.*, 1994, 14(5):407-414.

A – 50 µg/ml
B – 100 µg/ml
C – 200 µg/ml

CASEIN KINASE 2 ANTISENSE THERAPY

CROSS REFERENCE TO RELATED APPLICATIONS

This application is a continuation-in-part and claims the priority of PCT/US2005/045820 having an International Filing Date of Dec. 14, 2005, which claims priority under 35 U.S.C. 119(e) of U.S. Application Nos. 60/636,299 and 60/657,049 having filing dates of Dec. 14, 2004 and Feb. 28, 2005, respectively. This application also claims priority under 35 U.S.C. 119(e) of U.S. Application No. 60/898,674 filed Feb. 1, 2007 and U.S. Application No. 60/944,028 filed Jun. 14, 2007. The disclosures of these applications are incorporated herein by reference.

FEDERALLY SPONSORED RESEARCH OR DEVELOPMENT

The U.S. Government has certain rights in this invention pursuant to Grant Nos. R43 CA 099336 and CA015062 awarded by National Institutes of Health (NIH).

TECHNICAL FIELD

This invention relates to cancer therapy, and more particularly to cancer therapy using casein kinase 2 antisense molecules.

BACKGROUND

Casein protein kinase 2 (CK2) is a ubiquitous protein serine/threonine kinase that has been implicated in multiple functions in the cell including the regulation of cell growth and proliferation as well as apoptosis (see, for example, Tawfic et al., 2001, *Histol. Histopathol.*, 16:573-82). CK2 is a highly conserved enzyme, and has been suggested to be essential for cell survival. The kinase is a heterotetramer consisting of two catalytic subunits ($\alpha$ and/or $\alpha\alpha'$) complexed with two $\beta\beta$ subunits. One means by which CK2 regulates cell growth is through signaling in the nucleus where nuclear matrix and chromatin appear to be its preferential targets.

CK2 has been strongly implicated in the neoplastic process because of its elevated levels in various tumors. Studies involving transgenic expression of CK2 have provided evidence to suggest that modest overexpression of CK2$\alpha$ imparts an oneogenic potential to the cells, and further that the incidence of neoplasia is greatly enhanced in the presence of a second oncogenic signal.

SUMMARY

The invention provides for antisense oligonucleotides that hybridize to CK2 nucleic acid sequences and methods of using such antisense oligonucleotides to inhibit expression of CK2 and reduce the size of solid tumors.

This disclosure reports the effects of CK2$\alpha$ antisense delivered by different routes into prostate or bladder tumor xenografts. Prostate cancer xenograft in nude mice was generated using PC3-LN4 cells injected into the subcutis of mice. Intratumoral injection of the CK2$\alpha$ antisense oligonucleotide resulted in eradication of prostate cancer tumors in vivo in a dose and time dependent manner. An analysis of the tumors treated with CK2$\alpha$ antisense oligonucleotide demonstrated a downregulation of CK2 message and nuclear-associated activity. Under similar experimental conditions, normal cells and tissue were relatively resistant to the effect of CK2$\alpha$ antisense oligonucleotide with evidence of minimal apoptosis. Intravenous delivery of naked CK2$\alpha$ phosphorothioate antisense oligonucleotide to nude mice carrying the orthotopic prostate tumor can also effectively downregulate CK2, resulting in induction of apoptosis in the tumor. CK2$\alpha$ antisense oligonucleotides in the phosphodiester form encapsulated in sub 50 nm tenascin nanocapsules also were utilized. When delivered via the intravenous route, these nanoencapsulated formulations were found to be significantly more effective then the naked antisense oligonucleotide. Further, multi-specific sequences targeting both CK2$\alpha$ and CH2$\alpha'$ were found which have utility in both formulated and unformulated form.

In one aspect, the invention provides a method of inhibiting the expression of casein kinase 2 in a solid tumor. Such a method includes delivering an antisense oligonucleotide to the tumor, wherein the antisense oligonucleotide hybridizes to casein kinase 2 nucleic acid sequences and reduces the expression thereof.

In another aspect, the invention provides a method of reducing the size of a solid tumor in an individual. Such a method includes delivering an antisense oligonucleotide to the tumor, wherein the antisense oligonucleotide hybridizes to casein kinase 2 nucleic acid sequences and reduces the expression thereof. Generally, a reduction in expression of casein kinase 2 results in a reduction in size of the tumor.

Methods of delivering a casein kinase 2 antisense oligonucleotide can include, for example, intratumorally or intravenously. Further, an antisense oligonucleotide can be encapsulated. In an embodiment of the invention, the antisense oligonucleotide is a phosphorothioate antisense oligonucleotide or a siRNA. A representative antisense oligonucleotide has the sequence shown in SEQ ID NO:1, SEQ ID NO:2 or SEQ ID NO:7. In another embodiment of the invention, the casein kinase 2 target is casein kinase 2-$\alpha'$ or a casein kinase 2-$\beta$. Representative solid tumors that can be treated by methods of the invention include those that originate in a location such as prostate, bladder, breast, liver, kidney, brain, head, or neck.

In yet another aspect, the invention provides a composition that includes an antisense oligonucleotide and a pharmaceutically acceptable carrier, wherein the antisense oligonucleotide hybridizes to casein kinase 2 nucleic acid sequences and reduces the expression thereof. Such a composition can be provided in an encapsulated form. In one embodiment, the composition can include an antisense oligonucleotide having the sequence shown in SEQ ID NO:1, SEQ ID NO:2, or SEQ ID NO:7.

In another aspect, the invention provides an antisense oligonucleotide of up to 50 nucleotides in length that includes a portion of at least 8 consecutive nucleotides of SEQ ID NOs: 3, 4 or 7, wherein the antisense oligonucleotide inhibits the expression of human casein kinase 2$\alpha$ and 2$\alpha'$.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the descrip-

DESCRIPTION OF DRAWINGS

Like reference symbols in the various drawings indicate like elements.

DETAILED DESCRIPTION

Figure 1:
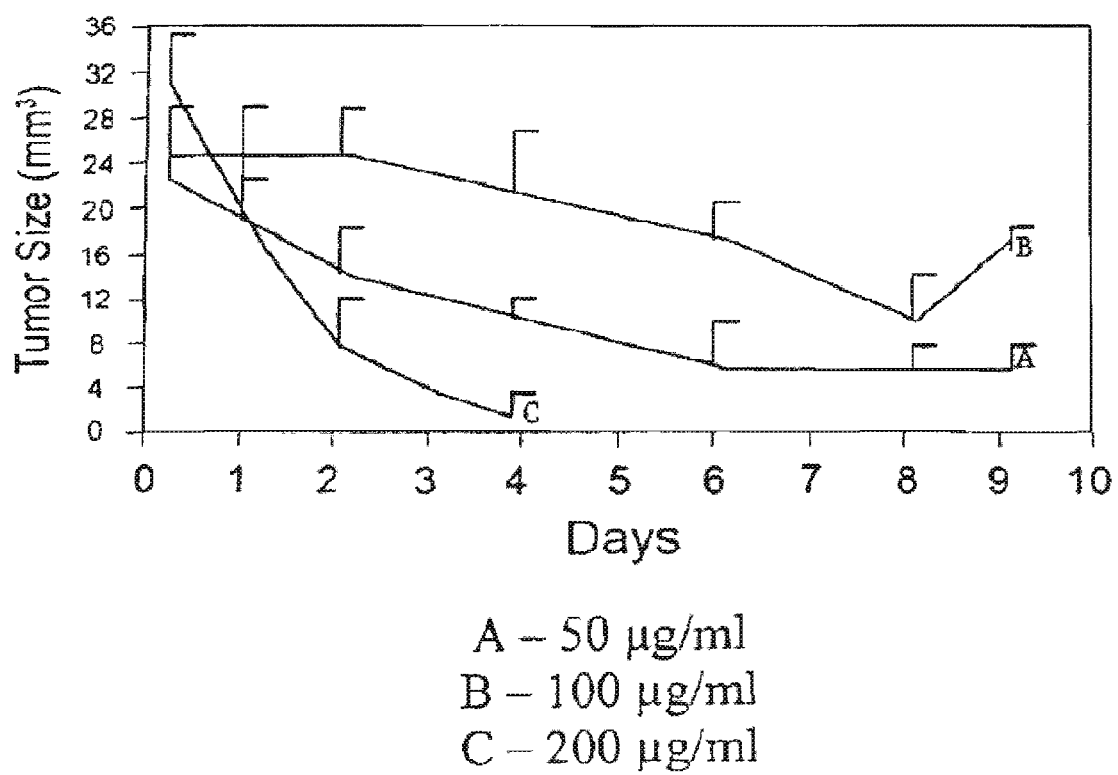
FIG. 1 is a graph showing prostate tumor size in athymic nude mice following intratumoral administration of a CK2 antisense oligonucleotide. Tumor size was assessed every 2 days. Each point represents 3 tumors.

The present invention employs antisense compounds, particularly oligonucleotides, to inhibit the expression of target nucleic acid molecules. As used herein, the term "target nucleic acid" refers to both RNA and DNA, including cDNA, genomic DNA, and synthetic (e.g., chemically synthesized) DNA. The target nucleic acid can be double-stranded or single-stranded (i.e., a sense or an antisense single strand). In some embodiments, the target nucleic acid encodes a casein kinase 2 (CK2) polypeptide. Thus, a "target nucleic acid" encompasses DNA encoding CK2, RNA (including pre-mRNA and mRNA) transcribed from such DNA, and also cDNA derived from such RNA. An "antisense" compound is a compound containing nucleic acids or nucleic acid analogs that can 1) specifically hybridize to a target nucleic acid to interfere with function, regulation or processing of the target nucleic acid, 2) specifically bind a protein to interfere with function of the target protein or 3) mimic pathogenic infection to engage cellular processes against a targeted nucleic acid species. Inhibition of expression of a target nucleic acid or protein by an antisense oligonucleotide is generally referred to as antisense technology. An antisense molecule thus includes siRNAs, antagomirs, aptamers and sequences complementary to an mRNA or any other target RNA, DNA or protein.

The term "hybridization," as used herein, means hydrogen bonding, which can be Watson-Crick, Hoogsteen, or reversed Hoogsteen hydrogen bonding, between complementary nucleoside or nucleotide bases. For example, adenine and thymine, and guanine and cytosine, respectively, are complementary nucleobases (often referred to in the art simply as "bases") that pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide in a target nucleic acid molecule, then the oligonucleotide and the target nucleic acid are considered to be complementary to each other at that position. The oligonucleotide and the target nucleic acid are complementary to each other when a sufficient number of corresponding positions in each molecule are occupied by nucleotides that can hydrogen bond with each other. Thus, "specifically hybridizable" is used to indicate a sufficient degree of complementarity or precise pairing such that stable and specific binding occurs between the oligonucleotide and the target nucleic acid.

It is understood in the art that the sequence of an antisense oligonucleotide need not be 100% complementary to that of its target nucleic acid to be specifically hybridizable. An antisense oligonucleotide is specifically hybridizable when (a) binding of the oligonucleotide to the target nucleic acid interferes with the normal function of the target nucleic acid, and (b) there is sufficient complementarity to avoid non-specific binding of the antisense oligonucleotide to non-target sequences under conditions in which specific binding is desired, i.e., under conditions in which in vitro assays are performed or under physiological conditions for in vivo assays or therapeutic uses.

Stringency conditions in vitro are dependent on temperature, time, and salt concentration (see, e.g., Sambrook et al., *Molecular Cloning: A Laboratory Manual*, Cold Spring Harbor Laboratory Press, NY (1989)). Typically, conditions of high to moderate stringency are used for specific hybridization in vitro, such that hybridization occurs between substantially similar nucleic acids, but not between dissimilar nucleic acids. Specific hybridization conditions are hybridization in 5×SSC (0.75 M sodium chloride/0.075 M sodium citrate) for 1 hour at 40° C., followed by washing 10 times in 1×SSC at 40° C. and 5 times in 1×SSC at room temperature.

In vivo hybridization conditions consist of intracellular conditions (e.g., physiological pH and intracellular ionic conditions) that govern the hybridization of antisense oligonucleotides with target sequences. In vivo conditions can be mimicked in vitro by relatively low stringency conditions. For example, hybridization can be carried out in vitro in 2×SSC (0.3 M sodium chloride/0.03 M sodium citrate), 0.1% SDS at 37° C. A wash solution containing 4×SSC, 0.1% SDS can be used at 37° C., with a final wash in 1×SSC at 45° C.

The specific hybridization of an antisense molecule with its target nucleic acid can interfere with the normal function of the target nucleic acid. For a target DNA nucleic acid, antisense technology can disrupt replication and transcription. For a target RNA nucleic acid, antisense technology can disrupt, for example, translocation of the RNA to the site of protein translation, translation of protein from the RNA, splicing of the RNA to yield one or more mRNA species, and catalytic activity of the RNA. The overall effect of such interference with target nucleic acid function is, in the case of a nucleic acid encoding CK2, inhibition of the expression of CK2. In the context of the present invention, "inhibiting expression of CK2" means to disrupt the transcription and/or translation of CK2 nucleic acid sequences resulting in a reduction in the level of CK2 polypeptide or a complete absence of CK2 polypeptide.

Identification of Target Sequences for CK2 Antisense Oligonucleotides

Antisense oligonucleotides are preferably directed at specific targets within a CK2 nucleic acid molecule. A representative CK2-α sequence from mouse can be found in GenBank Accession No. NM 009974; representative CK2-α sequences from human can be found in GenBank Accession Nos. NM 001892, S72393, and X70251; and representative CK2-β sequences from human can be found in GenBank Accession No. NM 001320. Representative CK2 antisense oligonucleotides are disclosed herein as well as in U.S. Publication No. 2002/0147163.

The targeting process includes the identification of a site or sites within the CK2 nucleic acid molecule where an antisense interaction can occur such that a desired effect, e.g., inhibition of CK2 expression, will result. Traditionally, preferred target sites for antisense oligonucleotides have included the regions encompassing the translation initiation or termination codon of the open reading frame (ORF) of the gene. In addition, the ORF has been targeted effectively in antisense technology, as have the 5' and 3' untranslated regions. Furthermore, antisense oligonucleotides have been successfully directed at intron regions and intron-exon junction regions.

Simple knowledge of the sequence and domain structure (e.g., the location of translation initiation codons, exons, or introns) of a target nucleic acid, however, is generally not sufficient to ensure that an antisense oligonucleotide directed to a specific region will effectively bind to and inhibit transcription and/or translation of the target nucleic acid. In its native state, an mRNA molecule is folded into complex secondary and tertiary structures, and sequences that are on the interior of such structures are inaccessible to antisense oligonucleotides. For maximal effectiveness, antisense oligonucleotides can be directed to regions of a target mRNA that are most accessible, i.e., regions at or near the surface of a folded mRNA molecule. Accessible regions of an mRNA molecule can be identified by methods known in the art, including the use of RiboTAG™, or mRNA Accessible Site Tagging (MAST), technology. RiboTAG™ technology is disclosed in PCT Application Number SE01/02054.

CK2 Antisense Oligonucleotides

Once one or more target sites have been identified, antisense oligonucleotides can be synthesized that are sufficiently complementary to the target (i.e., that hybridize with sufficient strength and specificity to give the desired effect). In the context of the present invention, the desired effect is inhibiting the expression of CK2 such that cellular levels of CK2 are reduced. The effectiveness of an antisense oligonucleotide to inhibit expression of a target nucleic acid can be evaluated by measuring levels of CK2 mRNA or protein using, for example, Northern blotting, RT-PCR, Western blotting, ELISA, or immunohistochemical staining. A description of anti-CK2 antibodies can be found, for example, in Faust et al. (1999, *Int. J. Biochem. Cell. Biol.*, 31:941-9), Nastaincyzyk et al. (1995, *Hybridoma*, 14:335-9) and references therein.

In some embodiments, it may be useful to target multiple accessible regions of a target nucleic acid. In such embodiments, multiple antisense oligonucleotides can be used that each specifically hybridize to a different accessible region. Multiple antisense oligonucleotides can be used together or sequentially. In some embodiments, it may be useful to target multiple accessible regions of multiple target nucleic acids.

In one aspect, a portion of the CK2α coding sequence has been identified that is highly homologous to the CH2α' coding sequence and is, therefore, useful for preparing multi-specific sequences that target both CK2α and CH2α'. Since it is known that either the α or α' subunit of the CK2 enzyme may substitute for the other in forming the α-α-β-β quaternary unit, it is advantageous to inhibit both functionally-equivalent subunits at the same time in order to prevent one type of alpha kinase unit from substituting for the other. A region that is homologous between CK2α and CK2α' is shown herein as SEQ ID NO:3, the reverse complement of which is shown herein as SEQ ID NO:4. This region corresponds to the 3' region of exon 7 in human CH2α (see, for example, positions 17,600-17,641 of GenBank Accession No. X69951), and to a portion of exon 8 in human CH2α'. A representative antisense oligonucleotide from this region is shown in SEQ ID NO:7.

In Example 6, it is shown that the bispecific SEQ ID NO:7 is more efficacious at reducing growth of carcinoma cells in vitro than a selection of other sequences available, both mono and bispecific. It is further shown that the improvement afforded by SEQ ID NO:7 is not dependent on medicinal chemistry, regardless of whether the sequence and the comparators were executed as unmodified phosphodiester DNA oligos, phosphodiester RNA chimeric oligos or double-stranded, RNA siRNA oligos. In Example 7, it is shown that, at a dose of 2×0.01 mg/kg, SEQ ID NO:7, targeted against SEQ ID NO:3, shows anti-tumor activity in mice, while a sequence targeted against only CK2a has no effect. While the Examples show that SEQ ID NO:7 is an effective inhibitor of CK2 and tumor growth, Table 1 below identifies some additional useful oligonucleotides from the region defined by SEQ ID NO:3.

TABLE 1

Useful oligonucleotides from CK2a region defined by SEQ ID NO:3

| | Antisense Sequence (5' to No.3') | Target Sequence |
|---|---|---|
| 13 | CATACTTGCCAGCATACAAC | 932-951 of NM 1895 |
| 14 | TACTTGCCAGCATACAACCC | 930-949 of NM 1895 |
| 15 | ACTTGCCAGCATACAACCCA | 929-948 of NM 1895 |
| 16 | CTTGCCAGCATACAACCCAA | 928-947 of NM 1895 |
| 17 | AGCCCAAACTCCACATGTCC | 784-803 of NM 1896 |
| 18 | AUACAGCCCAAACUCCACA | 789-807 of NM 1896 |
| 19 | UACAGCCCAAACUCCACAU | 788-806 of NM 1896 |
| 20 | ACAUACAGCCCAAACUCCA | 791-809 of NM 1896 |
| 21 | AAACUCCACAUAUCCAAAC | 911-929 of NM 1895 |
| 22 | CAUACAACCCAAACUCCAC | 921-939 of NM 1895 |
| 23 | AGCAUACAACCCAAACUCC | 923-941 of NM 1895 |
| 24 | CUUGCCAGCAUACAACCCA | 929-947 of NM 1895 |
| 25 | ACUUGCCAGCAUACAACCC | 930-948 of NM 1895 |
| 26 | UACUUGCCAGCAUACAACC | 931-949 of NM 1895 |
| 27 | AUACUUGCCAGCAUACAAC | 932-950 of NM 1895 |
| 28 | AUCAUACUUGCCAGCAUAC | 935-953 of NM 1895 |
| 29 | AUACUUGCCAGCAUACAAC | 932-950 of NM 1895 |

Useful sequences of about 16-25 nucleotides in length or less can be constructed that have homology to this region. Antisense sequences may be executed in either a single-stranded or double-stranded format. If, for example, one wanted to prepare a double-stranded, siRNA construct, the sense portion of the siRNA construct could be the target sequence together with a 3 prime dTdT overhang while the antisense strand would be as described with a 3 prime dTdT overhang. It is to be understood and is well-known in the art that many medicinal chemistry changes and substitutions are possible for purposes of increasing stability and binding affinity, e.g., dTdT overhangs may be substituted by a "UU" series. It is also to be understood that single-stranded species comprised at least in part of RNA may function as siRNA antisense strands or may be expressed from a plasmid vector. Further discussion on these topics may be found in Pei et al. (2006, *Nature Methods,* 3(9):670-6), Cullen (2006, *Nature Methods,* 3(9):677-81), Wiznerocicz et al. (2006, Nature Methods, 3(9):682-88), and Snove et al. (2006, *Nature Methods,* 3(9):689-695), which are incorporated herein by reference.

The antisense oligonucleotides in accordance with this invention can be from about 10 to about 50 nucleotides in length (e.g., 12 to 40, 14 to 30, or 15 to 25 nucleotides in length). Antisense oligonucleotides that are 15 to 23 nucleotides in length are particularly useful. However, an antisense oligonucleotide containing even fewer than 10 nucleotides (for example, a portion of one of the preferred antisense oligonucleotides) is understood to be included within the present invention so long as it demonstrates the desired activity of inhibiting expression of CK2.

An "antisense oligonucleotide" can be an oligonucleotide as described herein. The term "oligonucleotide" refers to an oligomer or polymer of ribonucleic acid (RNA) or deoxyribonucleic acid (DNA) or analogs thereof. This term includes oligonucleotides composed of naturally occurring nucleobases, sugars and covalent internucleoside (backbone) linkages, as well as oligonucleotides having non-naturally occurring portions which function similarly. Such modified or substituted oligonucleotides are often preferred over native forms because of desirable properties such as, for example, enhanced cellular uptake, enhanced affinity for a nucleic acid target, and increased stability in the presence of nucleases.

It should be noted that an antisense oligonucleotide may consist essentially of a nucleotide sequence that specifically hybridizes with an accessible region in the target nucleic acid. Such antisense oligonucleotides, however, may contain additional flanking sequences of 5 to 10 nucleotides at either end. Flanking sequences can include, for example, additional sequences of the target nucleic acid, sequences complementary to an amplification primer, or sequences corresponding to a restriction enzyme site.

For maximal effectiveness, further criteria can be applied to the design of antisense oligonucleotides. Such criteria are well known in the art, and are widely used, for example, in the design of oligonucleotide primers. These criteria include the lack of predicted secondary structure of a potential antisense oligonucleotide, an appropriate G and C nucleotide content (e.g., approximately 50%), and the absence of sequence motifs such as single nucleotide repeats (e.g., GGGG runs).

While antisense oligonucleotides are a preferred form of antisense compounds, the present invention includes other oligomeric antisense compounds, including but not limited to, oligonucleotide analogs such as those described below. As is known in the art, a nucleoside is a base-sugar combination, wherein the base portion is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric molecule. The respective ends of this linear polymeric molecule can be further joined to form a circular molecule, although linear molecules are generally preferred. Within the oligonucleotide molecule, the phosphate groups are commonly referred to as forming the internucleoside backbone of the oligonucleotide. The normal linkage or backbone of RNA and DNA is a 3' to 5' phosphodiester linkage.

CK2 antisense oligonucleotides that are useful in the present invention include oligonucleotides containing modified backbones or non-natural internucleoside linkages. As defined herein, oligonucleotides having modified backbones include those that have a phosphorus atom in the backbone and those that do not have a phosphorus atom in the backbone. For the purposes of this specification, and as sometimes referenced in the art, modified oligonucleotides that do not have a phosphorus atom in their internucleoside backbone also can be considered to be oligonucleotides.

Modified oligonucleotide backbones can include, for example, phosphorothioates, chiral phosphorothioates, phosphorodithioates, phosphotriesters, aminoalkylphosphotriesters, methyl and other alkyl phosphonates (e.g., 3'-alkylene phosphonates and chiral phosphonates), phosphinates, phosphoramidates (e.g., 3'-amino phosphoramidate and aminoalkylphosphoramidates), thionophosphoramidates, thionoalkylphosphonates, thionoalkyl phosphotriesters, and boranophosphates having normal 3'-5' linkages, as well as 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included. References that teach the preparation of such modified backbone oligonucleotides are provided, for example, in U.S. Pat. Nos. 4,469,863 and 5,750,666.

CK2 antisense molecules with modified oligonucleotide backbones that do not include a phosphorus atom therein can have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. References that teach the preparation of such modified backbone oligonucleotides are provided, for example, in U.S. Pat. Nos. 5,235,033 and 5,596,086.

In another embodiment, a CK2 antisense compound can be an oligonucleotide analog, in which both the sugar and the internucleoside linkage (i.e., the backbone) of the nucleotide units are replaced with novel groups, while the base units are maintained for hybridization with an appropriate nucleic acid target. One such oligonucleotide analog that has been shown to have excellent hybridization properties is referred to as a peptide nucleic acid (PNA). In PNA compounds, the sugar-backbone of an oligonucleotide is replaced with an amide containing backbone (e.g., an aminoethylglycine backbone). The nucleobases are retained and are bound directly or indirectly to aza nitrogen atoms of the amide portion of the backbone. References that teach the preparation of such modified backbone oligonucleotides are provided, for example, in Nielsen et al., *Science* 254:1497-1500 (1991), and in U.S. Pat. No. 5,539,082.

Other useful CK2 antisense oligonucleotides can have phosphorothioate backbones and oligonucleosides with heteroatom backbones, and in particular $CH_2NHOCH_2$, $CH_2N(CH_3)OCH_2$, $CH_2ON(CH_3)CH_2$, $CH_2N(CH_3)N(CH_3)CH_2$, and $ON(CH_3)CH_2CH_2$ (wherein the native phosphodiester backbone is represented as $OPOCH_2$) as taught in U.S. Pat. No. 5,489,677, and the amide backbones disclosed in U.S. Pat. No. 5,602,240.

Substituted sugar moieties also can be included in modified oligonucleotides. CK2 antisense oligonucleotides of the invention can comprise one or more of the following at the 2' position: OH; F; O—, S—, or N-alkyl; O—, S—, or N-alkenyl; O—, S—, or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Useful modifications also can include $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(C_2)_nCH_3]_2$, where n and m are from 1 to about 10. In addition, oligonucleotides can comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocyloalkyl, heterocycloalkaryl, aminoalkylamino, polyalkylamino, substituted silyl, an RNA cleaving group, a reporter group, an intercalator, groups for improving the pharmacokinetic or pharmacodynamic properties of an oligonucleotide, and other substituents having similar properties. Other useful modifications include an alkoxyalkoxy group, e.g., 2'-methoxyethoxy (2'-$OCH_2CH_2OCH_3$), a dimethylaminooxyethoxy group (2'-$O(CH_2)_2ON(CH_3)_2$), or a dimethylaminoethoxyethoxy group (2'-$OCH_2OCH_2N(CH_3)_2$). Other modifications can include 2'-methoxy (2'-$OCH_3$), 2'-aminopropoxy (2'-$OCH_2CH_2CH_2NH_2$), or 2'-fluoro (2'-F). Similar modifications also can be made at other positions within the oligonucleotide, such as the 3' position of the sugar on the 3' terminal nucleotide or in 2'-5' linked oligonucleotides, and the 5' position of the 5' terminal nucleotide. Oligonucleotides also can have sugar mimetics such as cyclobutyl moieties in place of the pentofuranosyl group. References that teach the preparation of such substituted sugar moieties include U.S. Pat. Nos. 4,981,957 and 5,359,044.

Useful CK2 antisense oligonucleotides also can include nucleobase modifications or substitutions. As used herein, "unmodified" or "natural" nucleobases include the purine bases adenine (A) and guanine (G), and the pyrimidine bases thymine (T), cytosine (C), and uracil (U). Modified nucleobases can include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Other useful nucleobases include those disclosed, for example, in U.S. Pat. No. 3,687,808.

Certain nucleobase substitutions can be particularly useful for increasing the binding affinity of the antisense oligonucleotides of the invention. For example, 5-methylcytosine substitutions have been shown to increase nucleic acid duplex stability by 0.6 to 1.2° C. (Sanghvi et al., eds., *Antisense Research and Applications*, pp. 276-278, CRC Press, Boca Raton, Fla. (1993)). Other useful nucleobase substitutions include 5-substituted pyrimidines, 6-azapyrimidines and N-2, N-6 and O-6 substituted purines such as 2-aminopropyladenine, 5-propynyluracil and 5-propynylcytosine.

Antisense oligonucleotides of the invention also can be modified by chemical linkage to one or more moieties or conjugates that enhance the activity, cellular distribution or cellular uptake of the oligonucleotide. Such moieties include but are not limited to lipid moieties (e.g., a cholesterol moiety); cholic acid; a thioether moiety (e.g., hexyl-S-tritylthiol); a thiocholesterol moiety; an aliphatic chain (e.g., dodecandiol or undecyl residues); a phospholipid moiety (e.g., di-hexadecyl-rac-glycerol or triethyl-ammonium 1,2-di-O-hexadecyl-rac-glycero-3-H-phosphonate); a polyamine or a polyethylene glycol chain; adamantane acetic acid; a palmityl moiety; or an octadecylamine or hexylamino-carbonyl-oxycholesterol moiety. The preparation of such oligonucleotide conjugates is disclosed in, for example, U.S. Pat. Nos. 5,218,105 and 5,214,136.

It is not necessary for all nucleobase positions in a given antisense oligonucleotide to be uniformly modified. More than one of the aforementioned modifications can be incorporated into a single oligonucleotide or even at a single nucleoside within an oligonucleotide. The present invention also includes antisense oligonucleotides that are chimeric oligonucleotides. "Chimeric" antisense oligonucleotides can contain two or more chemically distinct regions, each made up of at least one monomer unit (e.g., a nucleotide in the case of an oligonucleotide). Chimeric oligonucleotides typically contain at least one region wherein the oligonucleotide is modified so as to confer, for example, increased resistance to nuclease degradation, increased cellular uptake, and/or increased affinity for the target nucleic acid. For example, a region of a chimeric oligonucleotide can serve as a substrate for an enzyme such as RNase H, which is capable of cleaving the RNA strand of an RNA:DNA duplex such as that formed between a target mRNA and an antisense oligonucleotide. Cleavage of such a duplex by RNase H, therefore, can greatly enhance the effectiveness of an antisense oligonucleotide.

The CK2 antisense oligonucleotides of the invention are synthesized in vitro and do not include antisense compositions of biological origin, except for oligonucleotides that comprise the subject antisense oligonucleotides and that have been purified from or isolated from biological material. Antisense oligonucleotides used in accordance with this invention can be conveniently produced through the well-known technique of solid phase synthesis. Equipment for such synthesis is commercially available from several vendors including, for example, Applied Biosystems (Foster City, Calif.). Any other means for such synthesis known in the art additionally or alternatively can be employed. Similar techniques also can be used to prepare modified oligonucleotides such as phosphorothioates or alkylated derivatives.

Methods for Using CK2 Antisense Oligonucleotides

The antisense oligonucleotides of the invention are useful for research and diagnostics, and for therapeutic use. For example, assays based on hybridization of antisense oligonucleotides to nucleic acids encoding CK2 can be used to evaluate levels of CK2 in a tissue sample. Hybridization of the antisense oligonucleotides of the invention with a nucleic acid encoding CK2 can be detected by means known in the art. Such means can include conjugation of an enzyme to the antisense oligonucleotide, radiolabeling of the antisense oligonucleotide, or any other suitable means of detection.

Those of skill in the art can harness the specificity and sensitivity of antisense technology for therapeutic use. Antisense oligonucleotides have been employed as therapeutic moieties in the treatment of disease states in animals, including humans. For therapeutic methods, the cells or tissues are typically within a vertebrate (e.g., a mammal such as a human).

The invention provides therapeutic methods for inhibiting the expression of CK2 in a solid tumor and reducing the size of the solid tumor. By these methods, antisense oligonucleotides in accordance with the invention are introduced intratumorally into a solid tumor to inhibit expression of CK2. The methods and compositions of the present invention can be used to kill cells, inhibit cell growth, inhibit metastasis, inhibit angiogenesis, or otherwise reverse or reduce the malignant phenotype of tumor cells. Significantly, the size of a solid tumor can be reduced by inhibiting the expression of CK2. Solid tumors that can be treated using methods of the invention include those tumors that originate in a location or body part such as prostate, breast, liver, kidney, brain, head, and neck.

The pharmaceutical compositions of the present invention can be administered, for example, intratumorally, intravenously or topically. Intratumoral administration can be rapid (e.g., by direct injection) or can occur over a period of time (e.g., by slow infusion). The pharmaceutical forms suitable for injection or infusion use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that the form is readily injectable via syringe. It must be stable under the conditions of manufacture and storage, and must be preserved against the contaminating action of microorganisms, such as bacteria and fungi.

The ability of a CK2 antisense oligonucleotide to inhibit expression of CK2 can be assessed, for example, by measuring levels of CK2 mRNA or protein in a subject before and after treatment. Methods for measuring mRNA and protein levels in tissues or biological samples are well known in the art and include Northern blotting, Western blotting, in situ hybridization, and immunohistochemical staining.

Methods for formulating and subsequently administering therapeutic compositions are well known to those skilled in the art. See, for example, Remington, *The Science and Practice of Pharmacy*, 20$^{th}$ Ed., Gennaro & Gennaro, eds., Lippincott, Williams & Wilkins (2000). It is expected that the dosage for intratumoral injection will be determined more by the mass and density of the tumor than by the size of the patient. Dosing also can be dependent upon the severity and responsiveness of the tumor to be treated, with the course of treatment consisting of a single treatment to several days or several months of treatment, or until a cure is effected or a reduction in size of the tumor is achieved. Typically, the antisense oligonucleotide is administered in an inhibitory amount (i.e., in an amount that is effective for inhibiting the production of CK2 in the cells or tissues contacted by the antisense oligonucleotides). Thus, a single intratumoral injection of from about 2.5 µg to about 10 µg or greater of a CK2 antisense oligonucleotide can significantly reduce the size of a 3-5 mm tumor. Other amounts can be used for tumors of various tissue densities, sizes, and intercellular permeabilities. Persons of ordinary skill in the art routinely determine optimum dosages, dosing methodologies and repetition rates. Optimum dosages can vary depending on the relative potency of individual oligonucleotides, and can generally be estimated based on $EC_{50}$ found to be effective in in vitro and in vivo models. Following successful treatment, it may be desirable to have the patient undergo maintenance therapy to prevent subsequent enlargement of the tumor.

The present invention provides pharmaceutical compositions and formulations that include the CK2 antisense oligonucleotides of the invention. A "pharmaceutically acceptable carrier" (also referred to herein as an "excipient") is a pharmaceutically acceptable solvent, suspending agent, or any other pharmacologically inert vehicle for delivering one or more therapeutic compounds (e.g., CK2 antisense oligonucleotides) to a subject. Pharmaceutically acceptable carriers can be selected with intratumoral administration in mind so as to provide for the desired bulk, consistency, and other pertinent transport and chemical properties, when combined with one or more of therapeutic compounds and any other components of a given pharmaceutical composition. Typical pharmaceutically acceptable carriers that do not deleteriously react with nucleic acids include, by way of example and not limitation: water; saline solution; binding agents (e.g., polyvinylpyrrolidone or hydroxypropyl methylcellulose); fillers (e.g., lactose and other sugars, gelatin, or calcium sulfate); lubricants (e.g., starch, polyethylene glycol, or sodium acetate); disintegrates (e.g., starch or sodium starch glycolate); and wetting agents (e.g., sodium lauryl sulfate).

The CK2 antisense oligonucleotides of the invention further encompass any pharmaceutically acceptable salts, esters, or salts of such esters, or any other compound which, upon administration to an animal including a human, is capable of providing (directly or indirectly) the biologically active metabolite or residue thereof. Accordingly, for example, the invention provides pharmaceutically acceptable salts of CK2 antisense oligonucleotides. The term "pharmaceutically acceptable salts" refers to physiologically and pharmaceutically acceptable salts of the oligonucleotides of the invention (i.e., salts that retain the desired biological activity of the parent oligonucleotide without imparting undesired toxicological effects). Examples of pharmaceutically acceptable salts of oligonucleotides include, but are not limited to, salts formed with cations (e.g., sodium, potassium, calcium, or polyamines such as spermine); acid addition salts formed with inorganic acids (e.g., hydrochloric acid, hydrobromic acid, sulfuric acid, phosphoric acid, or nitric acid); salts formed with organic acids (e.g., acetic acid, citric acid, oxalic acid, palmitic acid, or fumaric acid); and salts formed from elemental anions (e.g., chlorine, bromine, and iodine).

Certain embodiments of the invention provide pharmaceutical compositions containing (a) one or more antisense oligonucleotides and (b) one or more other agents that function by a non-antisense mechanism. For example, anti-inflammatory drugs, including but not limited to nonsteroidal anti-inflammatory drugs and corticosteroids, and antiviral drugs, including but not limited to ribivirin, vidarabine, acyclovir and ganciclovir, can be included in compositions of the invention. Other non-antisense agents (e.g., chemotherapeutic agents) are also within the scope of this invention. Such combined compounds can be used together or sequentially to treat a solid tumor.

The antisense compositions of the present invention additionally can contain other adjunct components conventionally found in pharmaceutical compositions. Thus, the compositions also can include compatible, pharmaceutically active materials such as, for example, antipruritics, astringents, local anesthetics or anti-inflammatory agents, or additional materials useful in maintaining shelf life of the composition or maintaining integrity of the composition during storing or shipping, such as dyes, flavoring agents, preservatives, antioxidants, opacifiers, thickening agents, wetting agents, salts for influencing osmotic pressure, buffers, and stabilizers. When added, however, such materials should not unduly interfere with the biological activities of the antisense components within the compositions of the present invention. The formulations can be sterilized, if desired, provided sterilization does not deleteriously affect the nucleic acid(s) of the formulation.

Sub-50 nm Nanoparticles

As used herein, nanoparticles refer to stabilized surfactant micelles having an average diameter of less than about 50 nanometers (i.e., "sub-50 nm nanocapsules"). Nanoparticles and methods of making nanoparticles are described, for example, in U.S. Pat. No. 6,632,671. The nanoparticles described herein can be targeted to tumors by coating the sub-50 nm nanocapsules with at least one tumor-specific targeting moiety. "Coating" a nanocapsule with a targeting moiety refers to a non-covalent association between the nanocapsule and the targeting moiety.

Nanoparticles can be used to carry and deliver a cargo to tumors. A cargo moiety can be any of a number of different compounds or molecules for imaging or monitoring purposes or for therapeutic purposes including, but not limited to, a pharmaceutical agent. A "pharmaceutical agent" as used herein refers to any compound or molecule that can be used to treat tumors or complication of cancer. A pharmaceutical agent can include, for example, a polypeptide, a nucleic acid molecule (e.g., a construct encoding a polypeptide, or an antisense RNA, RNAi, or siRNA nucleic acid molecule), an antiviral agent, a drug or small molecule.

The following is a brief description of methods that can be used to make a tumor-targeted sub-50 nanoparticles as disclosed herein. The following description is meant to be representative only and is not meant to be limiting. In addition, the disclosure of U.S. Application No. 60/944,028 filed Jun. 14, 2007, which discloses the preparation of nanoparticles, is incorporated herein by reference. Briefly, a negatively-charged cargo moiety such as nucleic acid that is to be targeted and delivered to a tumor cell can be complexed with a polycationic polymer to condense or reduce its size to about 50 nm or less. A number of different polycationic polymers (also known as "condensing" agents or proteins) can be used and are well-known in the art. See, for example, Rolland (1998, *Crit. Rev. Therapeutic Drug Carr. Syst.*, 15:143-198). For example, enough polycationic condensing protein can be complexed with the negatively-charged cargo moiety to neutralize at least about 75% (e.g., about 80%, 85%, 90%, 95%, 99% or 100%) of the negatively-charged cargo moiety, which, for nucleic acids, can be measured by ethidium dye exclusion (see, for example, (1998, *J. Controlled Release*, 53:289-99). Simply by way of example, 125 µg of 10 kD polyornithine can be used to condense 500 µg of a 20-mer oligonucleotide or 87.5 µg of spermine may be used to condense 250 µg of a 14 kD siRNA oligo. For cargo moieties lacking a negative charge or bearing a positive charge, a condensing polycationic polymer may not be necessary.

An aqueous solution of the complexed or uncomplexed cargo moiety can be encapsulated by first dispersing the cargo moiety into a biocompatible, water-miscible solvent using a biocompatible, water-insoluble surfactant system suitable for preparation of an inverted or reverse micelle. Suitable surfactant systems are well-known in the formulation arts as amphillic materials that are essentially hydrophobic and characterized by a hydrophile-lipophile balance (HLB) of less than about 6, a critical micelle concentration (CMC) of less than about 200 µM, or a critical packing diameter greater than 1. Hydrophobic surfactants and hydrophobic, water-miscible solvents suitable for preparing reverse micelles are described in Pashley & Karaman (2004, In *Applied Colloid and Surface Chemistry*, John Wiley, pgs 60-85), Rosen (2004, in *Surfactants and Interfacial Phenomena*, John Wiley), *The Handbook of Industrial Surfactants* (1993, Ash, ed., Gower Pub), and *Perry's Chemical Engineer's Handbook* (1997, Perry & Green, 7th Ed., McGraw-Hill Professional). In one embodiment, a hydrophobic surfactant can be 2,4,7,9-tetramethyl-5-decyn-4,7-diol (TM-diol) used in a concentration of up to 0.5% by weight of surfactant micelle volume, and a water-miscible solvent can be DMSO. The concentration of surfactant selected should be sufficient to prepare an optically clear nanoemulsion but not so much as to induce aggregation, since aggregation can lead to overly large nanocapsules.

The micelles carrying the cargo moieties (i.e., nanocapsules) can be coated with tumor-targeting moieties (e.g., tenascin polypeptides) by mixing one or more targeting moieties with an aqueous dilution of the nanocapsules. Targeting moieties can be mixed with nanocapsules in a ratio (by weight) of about 1:100 to about 1:0.1 of nanocapsule to targeting moiety, depending upon the rate at which the nanocapsule is desired to dissolve or disassemble. In one embodiment, the coating weight ratio is 1:16 of nanocapsules to targeting moieties. Targeting moieties may also be modified by processes designed to enhance final nanoparticle function, e.g., tenascin polypeptides may be precipitated from cell culture supernatants using metal-containing ammonium sulfate such that metals known to promote oxidative stress are adsorbed onto coating ligands preceding nanoparticles preparation. Coating ligands may be readily modified with pharmaceutically acceptable heavy metals by re-precipitating protein in saturated ammonium sulfate solutions prepared with known levels of heavy metals. Incubation of about a 0.1-1 mg/ml solution of protein 1:2 with a saturated ammonium sulfate solution is most expeditiously executed for about 4-36 hours before recovering metal-modified coating ligand by centrifugation. Metal concentrations in the ultrapure ammonium sulfate may range from 1 part per thousand −1 part per trillion.

To stabilize the targeting moiety-adsorbed nanocapsule, the aqueous suspension of nanocapsules coated with one or more targeting moieties can be mixed into an aqueous solution of metal ions (i.e., a "stabilization solution") capable of precipitating, crystallizing, or iontophoretic exchange with the coated nanocapsules. Representative and non-limiting examples of solutes that can be used to precipitate the coated nanocapsules include ionic species derived from elements listed in the periodic table. Ions may be included in the aqueous stabilization composition in a range from 0.1 part per trillion to 1 Molar (M). An adequate amount of ion should be included such that the coated nanocapsules are sufficiently contacted with ions but not so much that aggregation occurs, which can lead to overly large capsules. In one embodiment, a stabilization solution can include about 10 millimolar (mM) $Ca^{2+}$ and about 200 mM $Li^+$. If ultrapure reagents are used in the stabilization solution, addition of very small amounts (e.g., less than 1 mM) of ions such as Ba, Fe, Mg, Sr, Pb and Zn, normally found in sufficient quantities in preparations of lithium and calcium salts that are not ultrapure, may be added to optimize stabilization of the coated nanocapsules. In one embodiment, a stabilization solution includes 10 mM $Ca^{2+}$, 200 mM $Li^+$, and 1-500 nM of $Sr^{+3}$ and $Mg^{+2}$. Nanocapsules that have a final surface charge as close to neutral as possible or even slightly negative and/or that have the morphology of a compact or roughly spheroidal shape are indications of optimized stability. Additionally, any other components that are capable of increasing the stability of the nanocapsules can be included as part of the stabilization solution such that the final dry mean diameter of the nanocapsules is between a range of 5-50 nm by AFM. Nanocapsules can be diluted into an aqueous solution of metal ions.

For a more consistent size of nanocapsules, the nanocapsules optionally can be atomized through a nozzle. Atomization should be sufficient to apply a shear force capable of breaking up flocculated aggregates without so much force as to induce hard aggregates. Those skilled in the art will understand that a particular nozzle diameter will lead to range of feed pressures suitable for atomizing the nanocapsules to a suitable and consistent size. In one embodiment, a nozzle diameter of less than about 250 microns with feed pressures of less than about 10 psi produces suitable nanocapsules. In some embodiments, the nanocapsules can be atomized into a stabilization solution.

The incubation time and temperature may be varied from about 8 hr to 7 days to vary the amount of time required for particle dissolution or disassembly in end use. After precipitating, atomizing, and/or incubating the nanocapsules in a stabilization solution, the nanocapsules can be filtered, centrifuged and/or dried to obtain separate and discrete sub-50 nm nanocapsules. In one embodiment, nanocapsules are incubated for 2 days at about 4° C. The resultant nanocapsules can be frozen or dried and reconstituted for later use.

Nucleic Acid Constructs

Nucleic acid constructs (e.g., a plasmid vector) are capable of transporting a nucleic acid into a host cell. Suitable host cells include prokaryotic or eukaryotic cells (e.g., bacterial cells such as *E. coli*, insect cells, yeast cells, and mammalian cells). Some constructs are capable of autonomously replicating in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell and are replicated with the host genome.

Nucleic acid constructs can be, for example, plasmid vectors or viral vectors (e.g., replication defective retroviruses, adenoviruses, and adeno-associated viruses). Nucleic acid constructs include one or more regulatory sequences operably linked to the nucleic acid of interest (e.g., a nucleic acid encoding a transcript that specifically hybridizes to a CK2 mRNA in its native form). With respect to regulatory elements, "operably linked" means that the regulatory sequence and the nucleic acid of interest are positioned such that nucleotide sequence is transcribed (e.g., when the vector is introduced into the host cell).

Regulatory sequences include promoters, enhancers and other expression control elements (e.g., polyadenylation signals). (See, e.g., Goeddel, *Gene Expression Technology: Methods in Enzymology*, 185, Academic Press, San Diego, Calif. (1990)). Regulatory sequences include those that direct expression of a nucleotide sequence in many types of host cells and that direct expression of the nucleotide sequence only in certain host cells (e.g., cell type- or tissue-specific regulatory sequences).

Articles of Manufacture

Antisense oligonucleotides of the invention can be combined with packaging material and sold as kits for inhibiting the expression of CK2. Components and methods for producing articles of manufacture are well known. The articles of manufacture may combine one or more of the antisense oligonucleotides set out in the above sections. In addition, the article of manufacture further may include buffers, hybridization reagents, or other control reagents for reducing and/or monitoring expression of CK2. Instructions describing how the antisense oligonucleotides can be used to inhibit expression of CK2 can be included in such kits.

The invention will be further described in the following examples, which do not limit the scope of the invention described in the claims.

EXAMPLES

Example 1

Intratumoral Administration of a CK2 Antisense Oligonucleotide

The effects of interfering with the CK2 signal in various cancer cell lines (ALVA-41, PC-3, LNCaP, and Ca9-22) was examined by employing antisense oligonucleotides against the α and β subunits of CK2. Results demonstrated that antisense CK2α and antisense CK2β elicit a potent apoptotic response in cells when cells were exposed to low concentrations of the antisense oligonucleotide. Results suggested that only a modest down regulation of CK2α is necessary to achieve a potent apoptotic response in cancer cells.

The ability of CH2α antisense oligonucleotides to ablate prostate tumors in vivo was determined. A metastatic human prostate cancer cell line, PC3-LN4 ($2 \times 10^6$ cells in 200 μl), was injected into the subcutis of athymic nude mice. The tumors were allowed to grow for 3 weeks until they reached 3-5 mm in size. Mice were randomized into 4 groups with 4 mice each. An antisense CK2α oligonucleotide [5'-cct gct tgg cac ggg tcc cga cat-3' (SEQ ID NO:1) (High Purity Salt Free, 1.0 umol scale, prepared by MWG Biotech, Highpoint, N.C.) phosphorothioate; 50 μl of a solution at a concentration of 50 or 200 μg/ml] was injected directly into the tumor on day 0, and the tumors were then observed for 7-10 days. A DNA oligonucleotide and saline were used as control treatments.

Treatment with the lower dose (2.5 μg) resulted in a 30-40% reduction in tumor size within 7 days after the second injection. Treatment with the higher dose (10 μg) resulted in a 95% reduction in tumor size by day 7, suggesting that relatively low doses of the CK2α antisense oligonucleotide were effective in inducing apoptosis in this model (Table 2). The experiment to assess tumor size was repeated every two days, and demonstrated a dose-dependent response to intratumoral therapy with a CK2 antisense oligonucleotide (FIG. 1).

To assess the effects of antisense CH2α, paraffin embedded tumor sections were stained with hematoxylin and eosin for histology analysis and for TUNEL for apoptosis analysis. Following staining, individual cancer cells were interspersed throughout necrotic and apoptotic stroma. Visual examination of the apoptotic cells in five different fields gave the values of 9±5 and 56±22 (percent apoptotic cells±S.D.) in nonsense vs., antisense-treated xenograft tumor, respectively. Reduction in CH2α signal was confirmed by immunoblotting and kinase activity assay (Slaton et al. *Mol. Can. Res.*, 2004; 2 (12):1-10). Therefore, intratumoral injection of the CK2α antisense oligonucleotide induced apoptosis in the prostate cancer xenograft model.

TABLE 2

| Therapy | Final Tumor Weight |
| --- | --- |
| Saline | 225 mg (200-530 mg) |
| Control oligonucleotides | 180 mg (220-460 mg) |

TABLE 2-continued

| Therapy | Final Tumor Weight |
|---|---|
| CK2 antisense (50 µg/ml) | 131 mg (125-290 mg) |
| CK2 antisense (200 µg/ml) | 30 mg (<10-55 mg) |

Example 2

Systemic Administration of Naked Antisense CK2α in an Orthotopic Model of Prostate Cancer Because intravenous administration is required to treat tumors which cannot be directly injected or distant metastases, the ability of CH2α antisense oligonucleotides to ablate prostate and bladder tumors in vivo following intravenous administration was determined. First, a metastatic human prostate cancer cell line, PC3-LN4 ($2 \times 10^6$ cells in 200 µl), was injected intraprostatically into male athymic nude mice. The tumors were allowed to grow for 3 weeks until they reached 6-8 mm in size. Mice were randomized into 3 groups with 3-4 mice each. An antisense CK2α oligonucleotide (5'-cct gct tgg cac ggg tcc cga cat-3' (SEQ ID NO:1) phosphorothioate; High purity Salt Free, 1.0 µmol scale, prepared by MWG Biotech, Highpoint, N.C.; 300 µg in 200 µl of saline or ~10 mg/kg) was injected by tail vein on day 0 and day 1, and the tumors were then observed for 7 days. A random sequence DNA oligonucleotide or saline were used in the control treatments. Tumors were collected 10 days after starting treatment, measured, weighed and scored for necrosis. Intravenous treatment with phosphorothioate-CK2α antisense oligonucleotide resulted in a 65% reduction in tumor volume 7 days after a second treatment, suggesting that CH2α was effective at reducing tumor size after only limited intravenous dosing (Table 3).

TABLE 3

Intravenous antisense CK2 therapy in an orthotopic prostate tumor model

| Therapy | Final Tumor Volume (mm³) | Final Tumor Weight (gm) | Necrosis Score |
|---|---|---|---|
| Saline | 1227 (320-2240) | 1.25 (0.2-2.3) | 1.33 (0-4) |
| Control oligonucleotides | 594 (407-800) | 0.93 (0.3-1.5) | 1.33 (0-2) |
| CK2 antisense naked | 425 (292-665) | 0.53 (0.3-0.9) | 0.33 (0-2) |

Necrosis scale: 0 = none, 1 = less than 5% of tumor area, 2 = <25% without central necrosis, 3 = <25% including central necrosis, 4 = >25% of tumor area including central necrosis.

As an additional control, the effect of antisense CK2α ODN in normal murine prostate was evaluated. The prostates of mice were injected orthotopically with either 20 µg of nonsense ODN (control) or 20 µg of antisense CK2α ODN phosphorothioates (treated) as described above. Mice were sacrificed at 7 days. Tissue sections of control and treated mice were stained for histology (H & E stain), apoptosis was detected by TUNL, and CK2α was detected by immunohistofluorescence. No differences in intact glandular architecture were observed in normal prostate treated with antisense CK2α compared to nonsense CH2α. Nor were any differences in CK2α immunosignal or any evidence of apoptosis observed in normal prostate treated with antisense CK2α.

Example 3

Preparation of Tumor-Targeted Nanoparticles

This example describes how colloidal formulations of the CK2 antisense sequences may be generated. Nanocapsules for therapeutic studies were prepared by the "dispersion atomization" method described in U.S. Pat. No. 6,632,671 with some modifications. Briefly, to prepare Formula A, 500 µg of phosphodiester oligonucleotide was first complexed with 125 µg of 10 kDa polyomithine (Sigma Chemical Co., St. Louis, Mo.), and dispersed into 150 µl of sterile water using a water-insoluble surfactant system (TM-diol, 7.5 µg in DMSO, SE-30 (Air Products)). Following emulsification with a water-miscible solvent (DMSO), the complexes were then inverted and diluted by the addition of 750 µl of PBS.

The resultant hydrophobic micelles were coated (non-covalently) by the addition of 12.5 µg of recombinant fibrinogen fragment of tenascin (TBG; prepared by the method of Aukhill et al. (1993, *J. Biol Chem.*, 268:2542-53) modified by a His-tag for column purification and re-precipitated in ultra-pure 40% ammonium sulfate containing 250 ppb $As^{+3}$ and 25 ppm $Se^{+4}$ for about 12.5 hours) then atomized into a LiCl salt receiving solution (135 mM $Li^+$, 9 mM $Ca^{2+}$, 1 nM $Sr^{2+}$, 100 nM $Mg^{2+}$ and 3 nM $Fe^{2+}$ (all ultrapure)). Following cold-room incubation (4° C.) with nominal rotation in 50 ml round-bottomed tubes for 14.5 hours, which stabilizes the coated micelles in the salt solution, the sub-50 nm nanocapsules were recovered by centrifugation at 20,000×g for 2 hrs and resuspended in PBS+10% sorbitol (at a concentration of 0.5 µg/µl) for filter sterilization through a 0.2 µm filter. In all formulations described, a small amount (1% of coating weight) of Sheep IgG was "spiked" into the ligand coat to enable immunodetection of nanocapsules uptake by anti-sheep IgG antibodies.

Average capsule size was less than 50 nm as measured by tapping mode atomic force microscopy using elliptical diameters of a 1 ng/ml sample dried down on a mica sheet. A surface charge of −1.5±5 mev was measured on a Zetasizer 4 Dynamic Light Scattering Device at a potential of 20 volts with a 2-second pause between measurements in 1 mM KCl at 2 µg/ml.

Formula B: sub-50 nm nanocapsules coated with TBG were generated as described in Formula A except that 6.3 mcg of TBG (re-precipitated in ultra-pure 40% ammonium sulfate containing 1.25 ppm $As^{+3}$ and 12.5 ppm $Se^{+4}$ and 50 ppb $Pb^{+2}$ for about 26 hours) was added to 500 mcg of Sequence 2 "asCK2" as phosphodiester oligo and condensed with 125 mcg of 10 kD polyomthine. When generating these nanocapsules, $Sr^{+3}$ and $Fe^{2+}$ were modified to 0 nM, $Mg^{2+}$ to 100 nM and $Pb^{2+}$ to 2.5 nM. Average capsule size was less than 50 nm as measured by tapping mode atomic force microscopy using elliptical diameters of a 1 ng/ml sample dried down on a mica sheet and a surface charge of −1.4±3.3 mev was measured on Zetasizer 4 dynamic light scattering device.

In later studies using Formula C, TBG was isolated and refolded from bacterial lysate by washing the insoluble pellet once with lysis buffer (50 mM Tris-HCl, 1.0 mM EDTA, 0.1 M NaCl, 0.2 mg/ml lysozyme, 0.1 % Triton X-100, and 0.1 mM PMSF, pH 8.0), containing 2 M urea and resuspending in 4M GuCl, 5 mM DTT in 0.02 M Tris-HCl, pH 8.0. After additional centrifugation, the clarified TBG solution was diluted with 2 M Guanidine-HCl, 20 mM Tris-HCl, pH 8.0 to make a final OD$_{280}$ of about 1 and diluted dropwise about 10-fold into 20 mM Tris-HCl, 0.2 M NaCl, 0.5 M Arginine-HCl, 10 µM CuCl$_2$ pH 8.0 for overnight stirred incubation (4° C.). After diafiltration against 20 mM Tris-HCl, pH 8.0 with an approximate 4-5 fold reduction in concentration and 0.45 µM filtration, a final purification was performed on heparin sepharose in 20 mM Tris-HCl, pH 8.0, with elution by bringing the NaCl concentration to 0.6 M.

Formula C: sub-50 nm nanocapsules coated with TBG were generated as described in Formula A except that 31.25 mcg of TBG (prepared as described above and reprecipitated in ultra-pure 40% ammonium sulfate containing 250 ppb As+3, 25 ppm Se+4, 2.5 ppm Hg+2 and 25 ppm Mo+5 for about 16 hours) was added to 500 mcg of SEQ ID NO:7 (phosphodiester 3' and propylendblocked—2OME RNA chimeric, LCK-6) and condensed with 125 mcg of 10 kD polyomthine. When generating these nanocapsules, the Sr+3 in the stabilization solution was modified to 10 nM and the Mg2+ was modified to 2.3 nM and capsules were incubated for 48 hours before centrifugation. Capsules were resuspended following centrifugation in PBS+10% Lactitol. Average capsule size was less than 50 nm as measured by tapping mode atomic force microscopy using elliptical diameters of a 1 ng/ml sample dried down on a mica sheet and a surface charge of −2.7±3 mev was measured on Zetasizer 4 dynamic light scattering device. Alternatively, this formulation may also be prepared in a stabilization solution where the Sr+3 in the stabilization solution is modified to 7.5 nM and the Mg2+ is modified to 2.3 nM before incubating the capsules for 48 hours before centrifugation.

Example 4

Systemic Administration of Nanoencapsulated Antisense CK2α in an Orthotopic Model of Prostate Cancer While delivery of antisense oligonucleotides can be given systemically, their efficacy has been limited by the inability to target tumor specifically. A delivery system has been developed by GeneSegues, Inc. (Chaska, Minn.) that involves encapsulation of molecular sized cargo into nanocapsules (sub 50 nm) coated with a ligand specific for receptors on neoplasms. PC3-LN4 ($2\times10^6$ cells in 200 μl) were injected intraprostatically into male athymic nude mice. The tumors were allowed to grow for 3 weeks until they reached 8-10 mm in size. An CK2α phosphodiester antisense oligonucleotide (SEQ ID NO:1; 300 μg in 200 μl of saline or ~10 mg/kg i.v.) was packaged as cargo into nanocapsules (Example 3, Formula A). This nanoencapsulated antisense CK2α was injected by tail vein on day 0 and day 1, and the tumors were then observed for 7 days. A DNA oligonucleotide and saline were used as control treatments. Tumors were collected 10 days after starting treatment and assessed (e.g., measured, weighed and scored) for necrosis (Table 4).

TABLE 4

| Therapy | Final Tumor Volume | Final Tumor Weight | Necrosis Score |
|---|---|---|---|
| CK2 antisense, formulated for protein-targeted, colloidal delivery | 947 (816-1122) $mm^3$ | 1.5 (1.2-1.9) g | 3.67 (3-4) |

Necrosis scale: 0 = none, 1 = less than 5% of tumor area, 2 = <25% without central necrosis, 3 = <25% including central necrosis, 4 = >25% of tumor area including central necrosis.

To assess the molecular effects of antisense CH2α, paraffin embedded tumor sections from Day 3 tumors (as treated with nanocapsules prepared according to Example 3, Formula B; about 10 mg/kg i.v. on Day 0 and 1) were analyzed by immunohistofluorescence for the presence of CH2α, histone deacetylase 1 (HDAC 1), activated Caspase 3 (aC3), and Cd 31(Pecam-1). Respectively, these proteins characterize the effect of antisense CK2α on its molecular target, the process of cellular differentiation, the process of apoptosis and the preponderance of tumor vasculature. HDAC1, a direct target of CK2, is an enzyme that acts upon chromatin to change the availability of chromosome binding sites to transcription factors. High HDAC1 activity corresponds to proliferative activity in cells and low activity is consistent with a program of terminal differentiation and cessation of growth. CK2 immunosignal was bright, nuclear and very uniform throughout the untreated tumor. Concomitantly, there was no evidence of apoptosis, differentiation/HDAC1 inhibition or anti-apoptosis as evidenced respectively by i) no elevation in activated caspase 3, ii) bright, uniform HDAC1 immunosignal, and iii) abundant presence of blood vessels detected by Cd31/Pecam-1. In remaining viable tumor regions, antisense CK2 effects a partial reduction in CK2 nuclear immunosignal concomitantly with an abrogation in HDAC 1 immunosignal, consistent with induction of tissue differentiation. These data indicate antisense CK2 is able to effect desirable molecular changes in tumor tissue after limited intravenous dosing.

While no evidence of apoptosis was observed following intravenous administration of antisense CH2α, administration of antisense CK2α formulated into a colloidal dosage form for enhanced delivery resulted in i) uniform reduction of CK2 nuclear immunosignal, ii) induction of apoptosis as indicated by uniform bright aC3 immunosignal, iii) maintenance of HDAC1 inhibition, and iv) anti-angiogenesis as evidenced by uniform reduction of tumor blood vessels. This induction of apoptosis following delivery enhancement was consistent with the appearance of significant central necrosis and fluid retention observed in nanocapsule-treated tumors at necropsy. Such results in an orthotopic model of prostate cancer are consistent with the apoptosis induction observed following intratumoral administration. Therefore, CK2α antisense oligonucleotide induced apoptosis in the prostate cancer xenograft model following intravenous administration.

Example 5

Inhibition of Mutant p53 by Intravenous Administration of Antisense CK2α

More than half of human tumors present with a mutation in the p53 tumor suppressor protein that renders it overly stable (Mutp53). By acting as a dominant mutant protein to activate multi-drug transporters (e.g. MDR-1) and multiple growth/survival cascades, the Mutp53 oncoprotein is believed to play a broad role in the phenomenon of drug resistance and the progression of advanced disease. Via direct protein binding, mutant p53 also inactivates wild-type p53, disabling the normal activation of apoptosis following significant cellular damage. Enhanced genomic instability in tumor cells is also highly correlated with Mutp53 and may be mediated by its direct binding to Topoisomerase 1 and concomitant down-regulation of the mismatch DNA repair enzyme, msh. Thus, the consequences of enhanced stability in this central protein to patients are resistance to chemotherapy, radiotherapy and poor prognosis.

An aggressive, human bladder cancer cell line, 253J-BV ($2\times10^6$ cells in 200 µl), was injected into the bladder of male athymic nude mice. The tumors were allowed to grow for 3 weeks until they reached 3-4 mm in size. Mice were randomized into 2 groups with 3-4 mice in each group. A CK2 phosphodiester antisense oligonucleotide (5'-gtc ccg aca tgt cag aca gg-3' (SEQ ID NO:2); Oligos, Etc., Wilsonville, Oreg.; 300 µg in 200 µl of saline or ~10 mg/kg) was nanoencapsulated (Example 3, Formula A) and injected intraperitoneally (i.p) on day 0 and day 3. The tumors were then observed for 7 days. A DNA nonsense oligonucleotide, similarly encapsulated, was used as a comparison. Tumors were collected 10 days after starting treatment and measured and weighed. Intravenous treatment with nanoencapsulated CK2α antisense oligonucleotide resulted in a significant 22% reduction in tumor volume 7 days after a second treatment. These experiments illustrate that antisense CH2α is effective at reducing the size of solid tumors in organs other than the prostate (Table 5).

TABLE 5

Intravenous antisense CK2 therapy in an orthotopic, bladder tumor model

| Therapy, formulated via targeted, colloidal delivery | Final Tumor Volume (mm³) | Final Tumor Weight (gm) |
|---|---|---|
| Nonsense oligonucleotides | 55 ± 2, SE (51-58) | 0.17 (0.1-1.2) |
| CK2 antisense oligonucleotides | 43 ± 2, SE (31-53) | 0.12 (0.1-1.0) |

CK2 is a prime regulator of p53 via direct protein binding in the C-terminus of p53. Protein binding is a mechanism of CK2 stabilization of cellular proteins. It has been shown in vitro by Guerra et al. (1997, *Oncogene*, 14:2863-8) that the isolated C-terminal region of p53 increases CK2 enzyme activity following binding direct binding to the oncoprotein. Using a pantropic, monoclonal antibody specific for both mutant and normal p53 (clone DO-1), paraffin-embedded sections were examined for p53 using immunohistofluorescence. Only mutant 53, but not wildtype p53, was detectable by immunohistofluorescence. A uniform abrogation of both CK2α nuclear immunosignal and p53 in tumors treated with antisense CK2α was observed relative to nonsense CH2α. Nuclear counterstaining for tissue treated with antisense CH2α was performed to confirm the presence of live tissue in antisense-treated tissue.

The reduction in both CK2α and p53 bladder xenograft tissue was confirmed by Western blotting. Tumors were pooled to create a single protein lysate for each treatment. These lysates were electrophoresed on a 4-12% acrylamide gel, transferred to nitrocellulose and CK2 was detected using a polyclonal chicken antibody that detects all 3 CK2 isoforms. A commercial rat cerebellum lysate was used as a positive control reference lane. Equivalent protein loading was confirmed using the Coomassie-stained gel. The Western blot showed that CK2α was reduced below the level of detection for this method for antisense-treated pooled lysate relative to the random oligonucleotide and saline-treated lysates. A reduction in both CH2α' and CK2β were observed, consistent with CK2α's role in stabilizing these structures.

p53 was detected using the pantropic, moloclonal DO-1. A pooled lysate of saline-treated bladder tumors was included as a comparison with the other pooled lysates. A recombinant, commercially-available p53 protein was used as a positive control. The protein contained a 7 kD fusion tag for a total molecular weight of 60 kD. Equivalent protein loading was confirmed using the Coomassie-stained gel. The Western blot showed that p53 was reduced by >70% relative to the nonsense-treated pooled lysate. p53 was markedly elevated in sense-treated lysates relative to the historical control. This result is consistent with both p53's and CH2α's role in mediating response to stress. Following stress such as administration of chemotherapy, it is known that tumor cells respond by increasing both CH2α activity and nuclear levels. Based on these results, intravenous administration of antisense CK2α reduces levels of mutant p53 in tumors.

Example 6

In vitro Comparison of Multispecific and Monospecific Antisense Sequences Against CK2

To identify effective antisense sequences that would inhibit CK2 actions, growth inhibition was assayed by thymidine incorporation in several SSCHN (squamous cell carcinoma of the head and neck) tumor lines in vitro in the presence of the antisense oligonucleotides shown in Table 6.

TABLE 6

Antisense sequences

| Name | Sequence (5'-3') (antisense or guide) | Chemistry | Target Region | Source | SEQ ID NO |
|---|---|---|---|---|---|
| ascK2 | gtc ccg aca tgt cag aca gg | Phosphodiester, 2'-O-methyl RNA 3'-chimeric | Translation start site of CK2a | Pepperkok et al, 1991, Exp Cell Res., 197:245-253 | 2 |
| CK2-740 | aag gtc ctg agc tac ttg tag | siRNA | Coding region, CK2a | | 5 |
| CK2-816 | aag tat gat ctt tcg gaa gga | siRNA | Coding region, CK2a | | 6 |
| LCK | ata caa ccc aaa ctc cac at | PO, chimeric, siRNA | 3'UTR of CK2aa' | | 7 |
| CK2-splice | tat ctc ttgt act cac ctt gag aat | morpholino | 3' end of exon 2 CK2a | | 8 |

TABLE 6-continued

Antisense sequences

| Name | Sequence (5'-3') (antisense or guide) | Chemistry | Target Region | Source | SEQ ID NO |
|---|---|---|---|---|---|
| A10 | uca aga uga cua cca gcu gdt dt | siRNA | Coding region, CK2a and CK2a' | Kinsella, 2005, | 9 |
| CK2mid | cag aau cuc aua cau gua a | siRNA | Coding region CK2a | | 10 |
| CR-4 | tgc tcc att gcc tct ctt gc | chimeric | Coding region, CK2A | US Application No. 10/958,999 | 11 |
| MasCK2 | atg tca gac agg ttg gcg gac aaa g | morpholino | 5' UTR of CK2a | Wang et al, 2005, | 12 |

RNA content of 3'-chimerics is designated by a number following a dash, e.g. - 6, and can optionally contain 3'-propyl or butyl endblocking.

Antisense sequences were administered to carcinoma cells in either one of two ways; 1) phosphodiester and chimeric sequences were administered from a concentrated stock of 800 μM in TE buffer to a final concentration of 1-3.75 μM or 2) siRNA sequences were complexed with Dotap according to the manufacturer's instructions (Roche Biochemicals) to a final concentration of 0.5 μM. Carcinoma cells were plated into 96- or 6-well plates pretreated with model tumor stroma (2:1 Tenascin:Fibronectin) at a concentration of 0.5 μg/cm$^2$ in cell-culture media (MEM, 0.5% fetal calf serum). Cells were treated for 48 hours with wells containing 1 μCurie of thymidine during the last 16-18 hours as an index of proliferation status. Proliferation indices from treated wells were calculated in reference to wells treated with either buffer or Dotap. Experiments were conducted in duplicate and repeated at least once.

Figure 2:
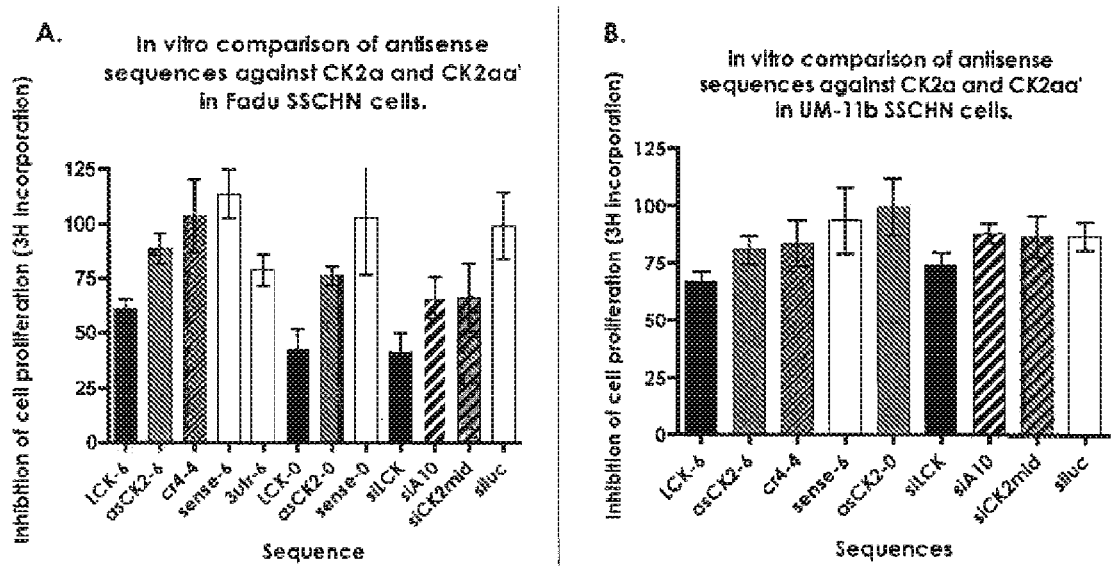
FIG. 2 are graphs that demonstrate that multi-specific antisense sequences show improvement in in vitro activity. Sequences (summarized in Table 5) were administered to carcinoma cells in vitro and growth rates were assessed by means of thymidine incorporation of 1 μCurie over a 16-24 hour period. siRNA sequences were administered via Dotap complexes prepared according to the manufacturer's instructions. Chimeric and phosphodiester sequences were not combined with lipids for delivery. Experiments were executed in duplicate using a 96 well format and repeated 1-2 times.

In the three SSCHN tumor cell lines tested, the LCK sequence provided the highest level of growth inhibition (for the RNA chimeric chemistry using SEQ ID NO:7, Fadu hyphopharynx: 61±4%, UM-11b larynx: 67±4%, SCC-15 tongue: 56±5%, mean±SE) and this effect was not dependent on sequence medicinal chemistry. Results are summarized in FIGS. 2A and 2B which shows that LCK-based sequences consistently inhibited tumor cell growth more strongly than other sequences made up in the same medicinal chemistry, regardless of the medicinal chemistry used. Antisense effects by unformulated phosphodiester and siRNA antisense sequences on CK2 protein levels was assayed by Western blotting following 24 hours of treatment and quantitated by densitometry as total CK2 (a, a' and β) relative to β-actin. Protein kinase CK2 plays a central role in mediating cellular responses to multiple stresses, e.g. following stress such as administration of chemotherapy, it is known that tumor cells respond by increasing both CH2α activity and nuclear levels (Wang, 2001). Relative to the increase in CK2 levels initiated by Dotap application, siLCK inhibited 57% of this increase, while another siRNA showed no inhibition of protein levels. Even the phosphodiester LCK inhibited 20% of the increase observed following the asCK2 sequence.

Example 7

In vivo Testing of Novel CK2 Antisense Sequences

Novel sequences were assayed in vivo for anti-tumor activity in several SSCHN xenograft tumor models. The usefulness of multi-specific sequences was assayed in vivo using SEQ ID NO:7, "LCK". Mice were inoculated intradermally in the flank with 3×10$^6$ cells of either the UM-11b or Fadu line. Both tumor lines are studied for their radioresistance. Additionally, the UM-11b line is highly inflammatory and immediately metastatic, while the Fadu line metastasizes later, but is mutant p53-(+) and highly chemoresistant. Mice were treated by i.v. injection with test article when tumors were 4-5 mm in diameter or ~50-100 mm$^3$ in volume. Local tumor volumes were followed by caliper measurements and are plotted in FIGS. 3A and 3B as mean values of 3-8 mice per group. In general, mice were administered 2 doses 48 hours apart. Sequences were executed as phosphodiester chimerics with 3' propyl endblocking (Trilink, San Diego, Calif.) and administered either in PBS ("naked") or formulated into tenfibgen-based nanoparticle (Example 1, Formula C).

A third SSCHN tumor model, SCC-15, was studied, but was found to be so metastatic that 5 of 8 controls (vs. 0 treated mice) died within 2 weeks from liver metastases. By whole-body luminescent imaging, tumor-free 6 month survival for the SCC-15 study group was as follows: 63% (1×50 mg/kg Example 1, Formula C), 50% (2×50 mg/kg Example 1, Formula C), 0% (10 mg/kg Docetaxel+2 mg/kg Cisplatin, 2 mg/kg Cisplatin q 24 hr), 11% (1×50 mg/kg, nanoparticles containing sense) and 0% (buffer).

Based on a pilot study using the phosphodiester Pepperkok sequence spanning the CK2α translation start site ("asCK2"), starting doses in the range of 25-50 mg/kg were chosen for nanoparticle-based sequences. In this range, Fadu (and SCC-15) tumors showed complete shrinkage or differentiation over a period of 3-4 weeks in a pilot study using the formulated phosphodiester Pepperkok sequence. UM-11b tumors only partially responded to the nanoparticle-formulated as CK2 sequence, which corresponded with UM-11b's higher expression of the less-common kinase subunit, CH2α'. However, in the UM-11b model, the unformulated LCK sequence utilizing a phosphodiester chimeric chemistry and addressing the coding region of both CK2a and a' (SEQ ID NO:7) surprisingly resolved small tumors by a necrotic mechanism over a period of 2 months at a dose of 2×25 mg/kg (~625 mcg, 5/5 mice, gray line with arrow, FIG. 3A). Typically, unformulated antisense sequences are cytostatic in mice as single agents (i.e., require chronic dosing to control or slow growth). Equivalent results were observed in the nanoparticle-formulated sequence albeit slower (8/8, dashed line and arrow, FIG. 3A). Tumor size was not immediately controlled in the high dose nanoparticle group (4/8, dashed line, FIG. 3A), indicating that lower dosing was more optimal, and tumor size was not controlled in mice administered with a nanoparticle-formulated sense sequence, indicating that a drug-mediated effect was extant.

Figure 3:
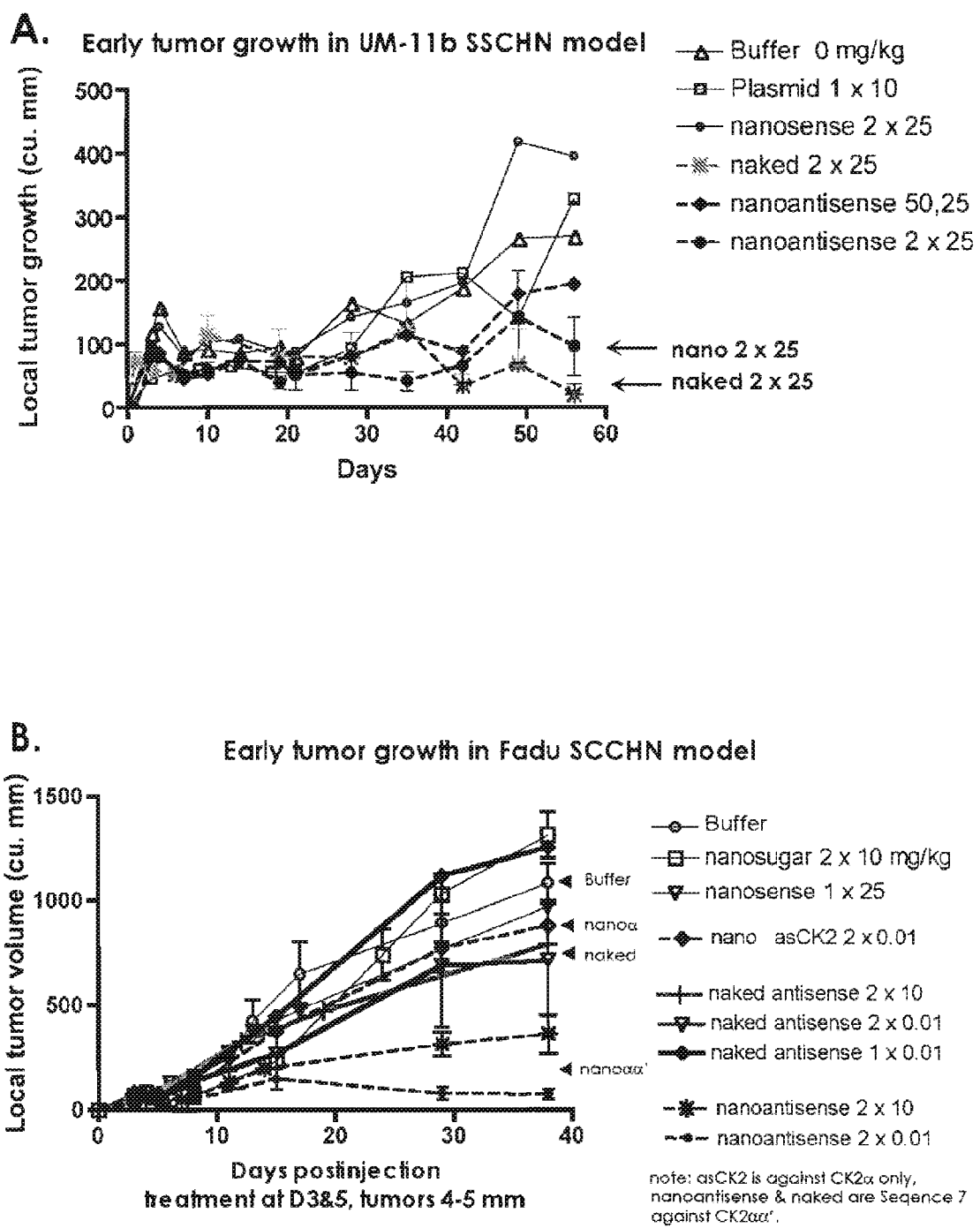
FIG. 3 are graphs that illustrate the improvement in inhibiting CK2 protein levels by the multi-specific sequences compared to monospecific sequences based on Western blotting of lysates from Fadu cells treated overnight with either 15 μM phosphodiester-based sequences delivered in PBS or 0.2 μM siRNA-based sequences administered in Dotap cationic lipoplexes. Experiments were performed 3 times. CK2 protein levels were calculated using densitometry to sum all 3 chains of the tetrametric protein and results were reported following normalization to beta-actin levels.

In the Fadu model, 25-50 mg/kg doses resulted in open wounds from rapidly dying tumors that were difficult to manage in immunocompromised mice. FIG. 3B summarizes tumor growth data from 0.01-10 mg/kg treatment groups. In this model at these dose ranges, the unformulated sequence showed only partial anti-tumor activity (1/10, thicker lines, see arrows). No growth inhibition was observed in mice treated with nanoparticle-formulated sugar or control sequence, nor was any activity observed in mice treated with 2×0.01 mg/kg (0.5 mcg) of the nanoparticle-formulated chimeric version of the Pepperkok sequence that had showed activity (with formulation) at 1×50 mg/kg (1250 mcg). The two lower dose nanoparticle groups showed early tumor control (dashed lines, see arrows). The lower dose group showed more desirable results in terms of complete resolution rather than mixed resolution and differentiation (0.5 mcg vs. 500 mcg; 3/3 vs. 4/8). These results indicate that novel antisense sequences to CK2 have significant anti-angiogenic and anti-tumor activity in vivo relative to currently available sequences.

Finally, the possibility of retreating mice with nanoencapsulated antisense CK2 was tested in 14 of the mice from the 3 SSCHN models that survived to 6 months. Mice were retreated with repeat doses ranging from 100 μg/kg to 100 ng/kg. Best results were achieved at lower doses in the range 100 ng/kg as evidence of tumor lysis syndrome was observed at μg/kg dosing (transient dehydration, fistulas from rapidly dying visceral metastases and organ fibrosis secondary to rapid necrotic tumor death). These mice had starting tumor dimensions of 15 mm in one dimension with liver, lung or brain metastases by whole-body imaging. In the 100 ng/kg dose group, 2/4 survived an additional 7 months following apparent clearance of liver metastases by whole-body imaging. These 2 mice had been flank-inoculated with the SCC-15 tumor (4 million cells) and previously treated with short-term chemotherapy (cisplatin+docetaxel). After 6 months, they were found to display signal by whole-body bioluminescence imaging using the Xenogen™ technique. For the Xenogen™ technique, mice were administered plasmid DNA encoding the luciferase reporter gene nanoencapsulated in tenfibgen, the purpose of which was to assess the existence of remaining tumor burden sensitive to tenfibgen uptake. After waiting 7 days to enable gene expression, mice were injected with D-luciferin contrast (the substrate for the expressed luciferin enzyme). Bioluminescence was then collected from anesthetised mice in the Xenogen™ apparatus to indicate the location of nanocapsule uptake, which in this case, was the tumor. During active treatment, mice were re-imaged every two weeks using exactly the same protocol with plasmid re-administered every 4 weeks. Plasmid administration was titered during method development so as to not negatively affect tumor growth.

In both cases of surviving mice, mice showed strong liver signal and in one mouse, some lymph node and kidney signal. After two to four weeks of thrice weekly 100 ng/kg intravenous injection of nanoencapsulated SEQ ID NO:7 (prepared in Example 3, Formula C), both mice were clear of liver, kidney and lymph node signal, and went on to live another 7 months before humane euthanasia due to advancing age. In the interest of time, following apparent clearance of visceral mets, the mice were treated with repeat i.p. dosing of the nanocapsules and 20 μg/kg cisplatin (and surgery for one mouse) to remove surface lesions. Occasional topical administration of a 3 μg/ml suspension of Formula C continued through the survival period. The two non-survivors of the low dose group died of complications from either surgery or a treatment-induced lung fistula from a dying met (without apparent lung fibrosis induction). Since, in these experiments, chemocombination before clearance of visceral mets had reliably induced tumor lysis complications in mice, it was concluded that regimens for treatment of visceral metastases should be different from those for surface lesions and addressed first in patient care. These data indicate that nanoencapsulated antisense CK2 have great promise for treating metastatic and disseminated cancer in aggressive, clinically relevant models at ultralow dosing.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of inhibiting the expression of casein kinase 2 in a solid tumor, comprising:
   delivering an antisense oligonucleotide to said tumor, wherein said antisense oligonucleotide has the sequence shown in SEQ ID NO:7.

2. The method of claim 1, wherein said antisense oligonucleotide hybridizes to casein kinase 2 nucleic acid sequences and reduces the expression thereof.

3. The method of claim 1, wherein said delivery is intratumorally, intravenously or topically.

4. The method of claim 1, wherein said antisense oligonucleotide is an encapsulated antisense oligonucleotide.

5. The method of claim 1, wherein said antisense oligonucleotide is a phosphorothioate antisense oligonucleotide.

6. The method of claim 1, wherein said antisense oliognucleotide is a siRNA.

7. The method of claim 1, wherein said casein kinase 2 is casein kinase 2α.

8. The method of claim 1, wherein said casein kinase 2 is casein kinase 2α'.

9. The method of claim 1, wherein said solid tumor originates in a location selected from the group consisting of prostate, bladder, breast, liver, kidney, brain, head, and neck.

10. A method of reducing the size of a solid tumor in an individual, comprising
    delivering an antisense oligonucleotide to said tumor, wherein said antisense oligonucleotide hybridizes to casein kinase 2 nucleic acid sequences and reduces the expression thereof, wherein said antisense oligonucleotide has the sequence shown in SEQ ID NO:7,
    wherein said reduction in expression of casein kinase 2 results in a reduction in size of said tumor.

11. A composition comprising an antisense oligonucleotide and a pharmaceutically acceptable carrier, wherein said antisense oligonucleotide hybridizes to casein kinase 2 nucleic acid sequences and reduces the expression thereof, wherein said antisense oligonucleotide has the sequence shown in SEQ ID NO:7.

12. The composition of claim 11, wherein said composition is encapsulated.

13. An antisense oligonucleotide of up to 50 nucleotides in length comprising a portion of at least 8 consecutive nucleotides of SEQ ID NO:7, wherein said antisense oligonucleotide inhibits the expression of human casein kinase 2α.

14. An antisense oligonucleotide of up to 50 nucleotides in length comprising a portion of at least 8 consecutive nucleotides of SEQ ID NO:7, wherein said antisense oligonucleotide inhibits the expression of human casein kinase 2α and 2α'.

15. The composition of claim 11, wherein said antisense oligonucleotide is a phosphodiester antisense oligonucleotide.

16. The antisense oligonucleotide of claim 13, wherein said antisense oligonucleotide is a phosphodiester antisense oligonucleotide.

17. The antisense oligonucleotide of claim 13, wherein said antisense oligonucleotide is encapsulated.

18. The antisense oligonucleotide of claim 13, further comprising a pharmaceutically acceptable carrier.

19. The antisense oligonucleotide of claim 14, wherein said antisense oligonucleotide is a phosphodiester antisense oligonucleotide.

20. The antisense oligonucleotide of claim 14, wherein said antisense oligonucleotide is encapsulated.

21. The antisense oligonucleotide of claim 14, further comprising a pharmaceutically acceptable carrier.

* * * * *

SEQUENCE LISTING

```
<160> NUMBER OF SEQ ID NOS: 29

<210> SEQ ID NO 1
<211> LENGTH: 24
<212> TYPE: DNA
<213> ORGANISM: Artificial Sequence
<220> FEATURE:
<223> OTHER INFORMATION: Oligonucleotide

<400> SEQUENCE: 1
cctgcttggc acgggtcccg acat                                            24

<210> SEQ ID NO 2
<211> LENGTH: 20
<212> TYPE: DNA
<213> ORGANISM: Artificial Sequence
<220> FEATURE:
```

```
<223> OTHER INFORMATION: Oligonucleotide

<400> SEQUENCE: 2
gtcccgacat gtcagacagg                                              20

<210> SEQ ID NO 3
<211> LENGTH: 55
<212> TYPE: DNA
<213> ORGANISM: Artificial Sequence
<220> FEATURE:
<223> OTHER INFORMATION: Oligonucleotide

<400> SEQUENCE: 3
gtttggatat gtggagtttg gttgtatgct ggcaagtatg atctttcgga aggag       55

<210> SEQ ID NO 4
<211> LENGTH: 41
<212> TYPE: DNA
<213> ORGANISM: Artificial Sequence
<220> FEATURE:
<223> OTHER INFORMATION: Oligonucleotide

<400> SEQUENCE: 4
catacttgcc agcatacaac ccaaactcca catatccaaa c                      41

<210> SEQ ID NO 5
<211> LENGTH: 25
<212> TYPE: DNA
<213> ORGANISM: Artificial Sequence
<220> FEATURE:
<223> OTHER INFORMATION: Oligonucleotide

<400> SEQUENCE: 5
aagguccuga gcuacuugta gdtdt                                        25

<210> SEQ ID NO 6
<211> LENGTH: 25
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (0)...(0)
<223> OTHER INFORMATION: DNA/RNA Molecule

<400> SEQUENCE: 6
aaguaugauc uuucggaagg adtdt                                        25

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide

<400> SEQUENCE: 7
atacaaccca aactccacat                                              20

<210> SEQ ID NO 8
<211> LENGTH: 25
<212> TYPE: DNA
<213> ORGANISM: Artificial Sequence
<220> FEATURE:
<223> OTHER INFORMATION: Oligonucleotide

<400> SEQUENCE: 8
```
tatctcttgt actcaccttg agaat                                    25

<210> SEQ ID NO 9
<211> LENGTH: 23
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (0)...(0)
<223> OTHER INFORMATION: DNA/RNA Molecule

<400> SEQUENCE: 9
ucaagaugac uaccagcugd tdt                                      23

<210> SEQ ID NO 10
<211> LENGTH: 19
<212> TYPE: RNA
<213> ORGANISM: Artificial Sequence
<220> FEATURE:
<223> OTHER INFORMATION: Oligonucleotide

<400> SEQUENCE: 10
cagaaucuca uacauguaa                                           19

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide

<400> SEQUENCE: 11
tgctccattg cctctcttgc                                          20

<210> SEQ ID NO 12
<211> LENGTH: 25
<212> TYPE: DNA
<213> ORGANISM: Artificial Sequence
<220> FEATURE:
<223> OTHER INFORMATION: Oligonucleotide

<400> SEQUENCE: 12
atgtcagaca ggttggcgga caaag                                    25

<210> SEQ ID NO 13
<211> LENGTH: 20
<212> TYPE: DNA
<213> ORGANISM: Artificial Sequence
<220> FEATURE:
<223> OTHER INFORMATION: Oligonucleotide

<400> SEQUENCE: 13
catacttgcc agcatacaac                                          20

<210> SEQ ID NO 14
<211> LENGTH: 20
<212> TYPE: DNA
<213> ORGANISM: Artificial Sequence
<220> FEATURE:
<223> OTHER INFORMATION: Oligonucleotide

<400> SEQUENCE: 14
tacttgccag catacaaccc                                          20

```
<210> SEQ ID NO 15
<211> LENGTH: 20
<212> TYPE: DNA
<213> ORGANISM: Artificial Sequence
<220> FEATURE:
<223> OTHER INFORMATION: Oligonucleotide

<400> SEQUENCE: 15
acttgccagc atacaaccca                                              20

<210> SEQ ID NO 16
<211> LENGTH: 20
<212> TYPE: DNA
<213> ORGANISM: Artificial Sequence
<220> FEATURE:
<223> OTHER INFORMATION: Oligonucleotide

<400> SEQUENCE: 16
cttgccagca tacaacccaa                                              20

<210> SEQ ID NO 17
<211> LENGTH: 20
<212> TYPE: DNA
<213> ORGANISM: Artificial Sequence
<220> FEATURE:
<223> OTHER INFORMATION: Oligonucleotide

<400> SEQUENCE: 17
agcccaaact ccacatgtcc                                              20

<210> SEQ ID NO 18
<211> LENGTH: 19
<212> TYPE: RNA
<213> ORGANISM: Artificial Sequence
<220> FEATURE:
<223> OTHER INFORMATION: Oligonucleotide

<400> SEQUENCE: 18
auacagccca aacuccaca                                               19

<210> SEQ ID NO 19
<211> LENGTH: 19
<212> TYPE: RNA
<213> ORGANISM: Artificial Sequence
<220> FEATURE:
<223> OTHER INFORMATION: Oligonucleotide

<400> SEQUENCE: 19
uacagcccaa acuccacau                                               19

<210> SEQ ID NO 20
<211> LENGTH: 19
<212> TYPE: RNA
<213> ORGANISM: Artificial Sequence
<220> FEATURE:
<223> OTHER INFORMATION: Oligonucleotide

<400> SEQUENCE: 20
acauacagcc caaacucca                                               19

<210> SEQ ID NO 21
<211> LENGTH: 19
<212> TYPE: RNA
<213> ORGANISM: Artificial Sequence
<220> FEATURE:
<223> OTHER INFORMATION: Oligonucleotide
```

<400> SEQUENCE: 21
aaacuccaca uauccaaac                                                        19

<210> SEQ ID NO 22
<211> LENGTH: 19
<212> TYPE: RNA
<213> ORGANISM: Artificial Sequence
<220> FEATURE:
<223> OTHER INFORMATION: Oligonucleotide

<400> SEQUENCE: 22
cauacaaccc aaacuccac                                                        19

<210> SEQ ID NO 23
<211> LENGTH: 19
<212> TYPE: RNA
<213> ORGANISM: Artificial Sequence
<220> FEATURE:
<223> OTHER INFORMATION: Oligonucleotide

<400> SEQUENCE: 23
agcauacaac ccaaacucc                                                        19

<210> SEQ ID NO 24
<211> LENGTH: 19
<212> TYPE: RNA
<213> ORGANISM: Artificial Sequence
<220> FEATURE:
<223> OTHER INFORMATION: Oligonucleotide

<400> SEQUENCE: 24
cuugccagca uacaaccca                                                        19

<210> SEQ ID NO 25
<211> LENGTH: 19
<212> TYPE: RNA
<213> ORGANISM: Artificial Sequence
<220> FEATURE:
<223> OTHER INFORMATION: Oligonucleotide

<400> SEQUENCE: 25
acuugccagc auacaaccc                                                        19

<210> SEQ ID NO 26
<211> LENGTH: 19
<212> TYPE: RNA
<213> ORGANISM: Artificial Sequence
<220> FEATURE:
<223> OTHER INFORMATION: Oligonucleotide

<400> SEQUENCE: 26
uacuugccag cauacaacc                                                        19

<210> SEQ ID NO 27
<211> LENGTH: 19
<212> TYPE: RNA
<213> ORGANISM: Artificial Sequence
<220> FEATURE:
<223> OTHER INFORMATION: Oligonucleotide

<400> SEQUENCE: 27
auacuugcca gcauacaac                                                        19

<210> SEQ ID NO 28

```
<211> LENGTH: 19
<212> TYPE: RNA
<213> ORGANISM: Artificial Sequence
<220> FEATURE:
<223> OTHER INFORMATION: Oligonucleotide

<400> SEQUENCE: 28
aucauacuug ccagcauac                                                19

<210> SEQ ID NO 29
<211> LENGTH: 19
<212> TYPE: RNA
<213> ORGANISM: Artificial Sequence
<220> FEATURE:
<223> OTHER INFORMATION: Oligonucleotide

<400> SEQUENCE: 29
auacuugcca gcauacaac                                                19
```